US010352683B2

(12) United States Patent
Ouellette

(10) Patent No.: US 10,352,683 B2
(45) Date of Patent: Jul. 16, 2019

(54) DEVICE FOR ANALYSIS OF SYNTHETIC ROPE OR CABLE, AND METHOD OF USE

(71) Applicant: Her Majesty the Queen in Right of Canada as Represented by the Minister of Natural Resources Canada, Ottawa (CA)

(72) Inventor: Sylvain Ouellette, Val-D'or (CA)

(73) Assignee: Her Majesty the Queen in Right of Canada as Represented by the Minister of Natural Resources Canada, Ottawa (CA)

( * ) Notice: Subject to any disclaimer, the term of this patent is extended or adjusted under 35 U.S.C. 154(b) by 257 days.

(21) Appl. No.: 15/301,131

(22) PCT Filed: Mar. 23, 2015

(86) PCT No.: PCT/CA2015/050221
§ 371 (c)(1),
(2) Date: Sep. 30, 2016

(87) PCT Pub. No.: WO2015/149165
PCT Pub. Date: Oct. 8, 2015

(65) Prior Publication Data
US 2017/0023347 A1 Jan. 26, 2017

Related U.S. Application Data

(60) Provisional application No. 62/093,542, filed on Dec. 18, 2014, provisional application No. 61/974,266, filed on Apr. 2, 2014.

(51) Int. Cl.
*G01N 27/82* (2006.01)
*G01B 7/04* (2006.01)
(Continued)

(52) U.S. Cl.
CPC ............. *G01B 7/046* (2013.01); *D07B 1/145* (2013.01); *G01N 27/82* (2013.01); *G01N 27/90* (2013.01);
(Continued)

(58) Field of Classification Search
CPC ........ G01N 27/82; G01N 27/83; G01N 27/90; G01N 27/9013; G01N 27/9026;
(Continued)

(56) References Cited

U.S. PATENT DOCUMENTS 5,804,964 A 9/1998 Hamelin et al.
9,335,318 B2 5/2016 Ilaka et al.
(Continued)

FOREIGN PATENT DOCUMENTS

EP 2589959 A2 5/2013
EP 2668127 B1 10/2014
(Continued)

OTHER PUBLICATIONS

Jomdecha C et al: "Design of modified electromagnetic main-flux for steel wire rope inspection", NDT & E International, Butterworth-Heinemann, Oxford, GB, vol. 42, No. 1, Jan. 1, 2009, pp. 77-83.

*Primary Examiner* — Huy Q Phan
*Assistant Examiner* — Raul J Rios Russo
(74) *Attorney, Agent, or Firm* — Banner & Witcoff, Ltd.

(57) ABSTRACT

Disclosed are methods and apparatuses for analysis of synthetic ropes, cords, slings, cables and belts (collectively termed "ropes") including but not limited to ropes for bearing loads as well as fiber optic cables. The ropes are provided with one or more elements for magnetic detection, wherein the magnetic detection elements each comprise a metal fiber or an appropriately treated synthetic fiber. The methods and apparatuses encompass detection of induced or residual magnetism or magnetic flux in the magnetic detec-
(Continued)

tion element(s), to sense for example lay length and/or damage, breakage or wear of the magnetic detection element(s), indicative of the condition of the rope.

26 Claims, 20 Drawing Sheets

(51) Int. Cl.
*G01N 27/90* (2006.01)
*D07B 1/14* (2006.01)
*G01N 27/83* (2006.01)

(52) U.S. Cl.
CPC ....... *G01N 27/904* (2013.01); *G01N 27/9013* (2013.01); *G01N 27/9026* (2013.01); *G01N 27/9033* (2013.01); *D07B 2301/555* (2013.01); *D07B 2301/5536* (2013.01); *G01N 27/83* (2013.01)

(58) Field of Classification Search
CPC .. G01N 27/9033; G01N 27/904; G01N 27/72; G01R 33/00; G01R 33/0035; G01R 33/0047; G01R 33/0322; G01R 33/0327; G01R 33/10; G01R 33/1284
USPC ... 324/51, 55, 200, 217, 219, 228, 233, 239, 324/240, 254, 257, 260
See application file for complete search history.

(56) References Cited

U.S. PATENT DOCUMENTS

| | | | |
|---|---|---|---|
| 2010/0043381 A1* | 2/2010 | Van Zyl | D07B 1/068 57/215 |
| 2010/0102807 A1* | 4/2010 | Yoshioka | G01N 27/83 324/240 |
| 2013/0147471 A1* | 6/2013 | Weischedel | G01N 27/83 324/238 |
| 2014/0266169 A1* | 9/2014 | Huntley | G01D 1/00 324/222 |
| 2015/0120215 A1* | 4/2015 | Padilla | G01N 29/07 702/34 |
| 2015/0285767 A1 | 10/2015 | Ouellette | |
| 2016/0169841 A1* | 6/2016 | Padilla | G01N 29/07 702/34 |

FOREIGN PATENT DOCUMENTS

| | | |
|---|---|---|
| EP | 2740702 B1 | 9/2015 |
| EP | 2740703 B1 | 9/2015 |
| EP | 2740704 B1 | 9/2015 |
| EP | 2740705 B1 | 9/2015 |
| JP | 2001-153845 A | 6/2001 |
| JP | 2003050230 A | 2/2003 |
| JP | 2005-512922 A | 5/2005 |
| JP | 2005156419 A | 6/2005 |
| WO | 2003/054290 A1 | 7/2003 |
| WO | 2012100938 | 8/2012 |
| WO | 2014/053047 A1 | 4/2014 |
| WO | 2015139842 | 9/2015 |

* cited by examiner

;
DEVICE FOR ANALYSIS OF SYNTHETIC ROPE OR CABLE, AND METHOD OF USE

FIELD OF THE INVENTION

This invention relates to the field of analysis and/or testing/monitoring of synthetic ropes, cables, slings, cords and belts. In particular the invention permits analysis of the integrity and load capacity of ropes, cables, slings, cords and belts with industrial applications, such as in mine hoisting operations. In other embodiments, the invention permits analysis of the integrity and function of fibre optic cables and the like.

BACKGROUND TO THE INVENTION

Ropes, cables and the like are used extensively for many purposes such as ropeways, cable cars, ski lifts, chairlifts, elevators, and military applications, but are of particular importance in the mining industry where the Intent is to use these for raising and lowering conveyances carrying personnel, equipment, material, waste and ore in underground operations, such as between the mining accesses and the surface. For such applications, ropes may have considerable length and must carry considerable loads, including the weight of the ropes themselves in the sections between the conveyances and the mine hoists at the surface (and underground as well) and used for their deployment.

One of the key concerns for all ropes is to determine when the rope is still in safe working condition or should be replaced. The costs to replace ropes can be very significant, and yet timely replacement is imperative to avoid excessive rope wear and rupture. To ensure operational safety and acceptable operational life of the system, the physical condition of such ropes must be monitored frequently, for example as required by specific regulations. For this reason, since industrial applications typically utilize wire ropes, previous efforts have focused upon devices and methods to test wire ropes for potential wear or deterioration. Some of these devices and methods have enabled on-site testing of the rope whilst in situ at the point of use, without causing damage or destruction to the rope. Such devices and methods are particularly advantageous as they minimize the impact of costly operational disruptions and stoppages. Wire ropes or cables and the like may thus be retained in situ for continued use (with periodic testing) until their safe operational life is substantially completed, for example if the rope parameters fall outside of regulatory requirements.

One important parameter to assess wire or synthetic rope condition, but not exclusively, is to test for "lay length". For example, wire ropes are made up of twisted or braided metal wires. Individual metal wires are twisted together to form bundles or strands, and then a number of such strands are twisted together to form a rope or cable. The lay length of such a rope is the distance along the rope (measured parallel to the centre line or axis of the rope) in which a strand at or beneath the surface makes one complete turn or helical spiral around or within the rope. Often, the lay length is measured over a few lay lengths and then the measurement is divided by the number of lay lengths to produce an average lay length value over the measured section. The lay length is known when the ropes is first manufactured (or at least after the strands have been allowed to settle into their more-permanent positions following a few lifting cycles) but it will change during use. For example, in mining applications the lay length changes with depth due to the torsional behavior of stranded hoist rope. These variations evolve over the life of the rope and must be monitored to ensure that they remain within established operational or safety parameters. Localized faults, wear, corrosion, core deterioration, strand breakage etc. may all cause increased lay length. The relevance of changes in lay length of a rope can require expert interpretation and/or precise monitoring. In general, if the lay length of a rope or cable and the like changes beyond defined limits, or if it changes locally, this may indicate potential failure of the rope, and the requirement for rope replacement.

Various testing methods are known for assessment of ropes. For example, in magnetic field testing a wire rope is brought into a magnetic field, and the presence of defects in the wire rope is detected through areas of induced flux changes. In other examples, eddy current testing comprises passing an alternating electrical current through a coil producing a magnetic field. When the coil is placed near a conductive material, the changing magnetic field induces closed loops of current flow known as eddy currents in the material, which produce their own magnetic fields that can be measured and used to determine the presence of flaws in the wire rope.

Synthetic ropes are in principle attractive for the replacement of wire ropes in numerous applications because they have a number of advantages over wire ropes including: higher strength to weight ratios, corrosion resistance, better fatigue life, and lower maintenance requirements. However, compared to wire ropes, it can be more difficult to assess local faults as well as the lay length of synthetic ropes as they are typically comprised of non-metallic substances not amenable to the aforementioned magnetic field techniques. Often, those testing or monitoring of synthetic ropes must rely upon visual inspection, or Imaging techniques to assess rope wear and integrity, which may be less reliable and may fail to provide an accurate assessment of broken strength-member fibres, lay length and/or rope condition. The problems associated with such inspection techniques may be further exacerbated by the use of non-load-bearing covers, which are sometimes applied to synthetic ropes to protect the strength member fibres of the synthetic rope from damage and/or UV radiation, but which otherwise obscure the strength-member fibres from visual inspection.

Thus, there remains a need in the art for devices and methods for analysis of synthetic ropes and cables. More particularly, the need extends to assessment of lay length of synthetic ropes and cables, and/or assessment of wear or damage including breakage of strength-member fibres of synthetic ropes or cables.

SUMMARY OF THE INVENTION

Certain embodiments provide an apparatus for measuring lay length of a synthetic rope comprising at least one magnetic detection element that completes one or more circumferential, helical or sinusoidal path(s) around or within the synthetic rope for each lay length of the rope, the apparatus comprising:
  a sensor device having a body defining an elongate passageway enabling the synthetic rope to be advanced there through in a direction of the central axis of the rope while permitting limited lateral movements of the rope;
  sensors on the body of the sensor device, sensing changes in magnetic flux in the region of the rope caused by variations in the magnetic flux of the at least one magnetic detection element and/or its proximity and to the sensors, thereby to generate an oscillating pattern of detected magnetic flux (e.g. residual magnetic flux) as the rope advances through the passageway;

means for associating the detected oscillations with physical distances along the rope; and a lay length calculator or display that calculates or displays a distance along the synthetic rope of one or more of the detected oscillations correlating to the number of circumferential or helical paths of the magnetic detection element around or within the rope.

Certain other embodiments provide for an apparatus for testing a synthetic rope comprising at least one magnetic detection element running the length of the synthetic rope, the apparatus comprising:

a sensor device having a body defining an elongate passageway enabling the synthetic rope to be advanced there through in a direction of the central axis of the rope while permitting limited lateral movements of the rope;

sensors on the body of the sensor device, sensing changes in magnetic flux in the region of the rope caused by breakage points or damage to the at least one magnetic detection element;

a calculator or display that calculates or displays recorded data corresponding to the changes in magnetic flux; and optionally means for preconditioning the at least one magnetic detection element by generating magnetic flux therein.

Certain other embodiments provide for a use of an apparatus as described herein, for testing a synthetic rope comprising at least one magnetic detection element, to assess at least one of: the integrity, the strength, the safety, the lifespan, the load capacity, or the wear of the rope.

Certain other embodiments provide for a use of an apparatus as described herein, to analyze a lay length of a synthetic rope, and/or to test for damage or breakage or elements of a synthetic rope.

Certain other embodiments provide for a method for testing a lay length of a synthetic rope comprising at least one magnetic detection element running through the rope, the method comprising the steps of:

applying an apparatus for testing lay length as described herein to the rope, so that the rope passes through the passageway of the sensor device;

advancing the rope through the passageway so that the sensors on the body of the sensor device sense changes in magnetic flux in the region of the rope caused by variations in the proximity and magnetic flux of the magnetic detection element to the sensors, thereby to generate an oscillating pattern of detected magnetic flux as the rope advances through the passageway;

associating the detected oscillations with physical distances along the rope; and calculating or displaying a lay length according to a distance along the synthetic rope of one or more of the detected oscillations correlating to the number of circumferential, helical, or sinusoidal paths of the magnetic detection element around or within the rope.

Certain other embodiments provide a method for testing a synthetic rope comprising at least one magnetic detection element running the length of the synthetic rope, for damage or breakage of component elements of the rope, the method comprising the steps of:

applying to the rope an apparatus as described herein, such that the rope passes through the elongate passageway;

advancing the rope through the passageway, the sensors sensing changes in magnetic flux in the region of the rope caused by breakage points or damage to the at least one magnetic detection element; and calculating or displaying data corresponding to the changes in magnetic flux indicative of said breakages or damage to the at least one magnetic detection element.

DETAILED DESCRIPTION OF EXEMPLARY EMBODIMENTS

Figure 1:
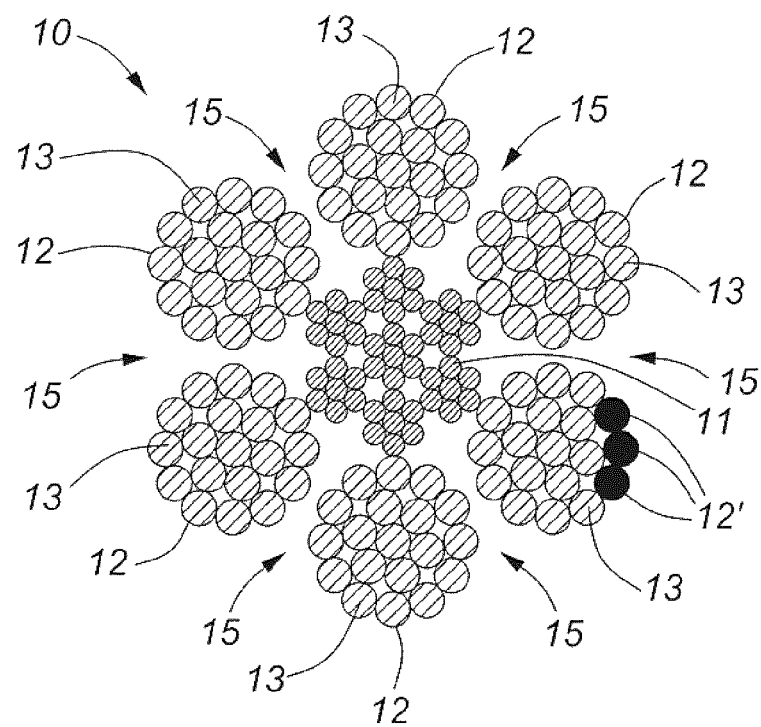
FIG. 1 illustrates a cross-sectional view of an example rope comprising magnetic detection elements. Although the basic construction of the rope illustrated is typical of a wire rope, the principles regarding lay length and the presence of a magnetic detection element nonetheless apply to synthetic ropes. The embodiment illustrated is exemplary, and in other embodiments the presence of one or more magnetic detection element may be masked by an additional cover or coating on the rope, or the magnetic detection element(s) may be concealed within a structure of the rope, for example by being woven into the rope without any portion exposed upon the rope exterior.

Synthetic ropes, cables, slings, cords and belts (collectively referred to herein as "ropes") can be used in many applications, including high risk applications where the safety of individuals is dependent upon the strength and integrity of the rope. Such ropes can also be used in the manufacture of other items and articles, such as but not limited to nets, webbing etc. Synthetic ropes typically include strength member elements, wherein a "strength member element" refers to any component of a rope, including a filament, fibre, strand or yarn, which provides or is intended to provide at least some degree of loading strength to the rope. "Synthetic rope": refers to any rope, cable, sling, cord, belts or the like comprising synthetic strength member elements of any synthetic material, which collectively confer load-bearing properties to the rope. Such synthetic ropes may comprise, for example, aramid, meta-aramid (Nomex), para-aramid such as para-oriented aromatic polyamides, condensation polymers of para-oriented aromatic diamine or para-oriented aromatic dicarboxylic acid halide, including but not limited to commercially available para-aramids such as Twaron®, Technora®, and Kevlar®, polybenzoxazole (PBO), liquid crystal polymer (LCP, such as Vectran™), polytetrafluoroethylene (PTFE), high modulus polyethylene (HMPE), polyamide (such as nylon), glass, polyester, polyethylene, polypropylene, or combinations thereof.

A rope is comprised of a plurality of Individual and typically fine filaments. A plurality of such filaments may form a "fibre". The filaments may be organized into longitudinally associated bundles, for example by plying or twisting the filaments or fibre together, thereby to produce a yarn or strand, which together with other yarns or strands, may be combined to form the rope. In any rope the strength member elements that work collectively for load bearing, or for communications such as fibre optic cables.

A rope as disclosed here may have any size, width or diameter, but typically may comprise in cross-section a widest dimension of from 2 mm to 500 mm. Moreover, a rope may have any form of cross section. Whilst a circular or substantially circular cross-section may be typical of many ropes, the ropes employed herein are not limited in this regard, and may alternatively have a non-circular cross-section, such as an oval, rectangular, square, triangular, or other cross-section. In the case for example of a "rope", that could be identified as sling, belt and even some typical nonstandard shape ropes may have a flat profile, such that the cross-section is long and thin. In this way, these may take the form of a tape of a typical belt-like configuration as is well known in the art.

Disclosed herein are accurate and reliable methods to test or analyze ropes, especially synthetic ropes, for the purposes of assessing their safety and suitability for continued operational use. In select embodiments such methods, and devices for conducting the methods, may be used even if the ropes are sheathed with non-load bearing covers or coatings. In this way, ropes may be tested quickly and efficiently even in their place of operational use, and if necessary replaced, with minimal operational down-time.

The testing methods, and corresponding devices for conducting the methods, require the use of ropes that comprise at least one "magnetic detection element". Synthetic ropes typically comprise multiple "strength member elements" that individually and collectively confer strength to the rope. Such elements may include for example filaments, fibres, strands or yarn, which provide or are intended to provide at least some degree of loading strength to the rope, especially when the elements are bound, twisted, platted, or otherwise associated together. In some embodiments, a "magnetic detection element" refers to one of those elements that is detectable by magnetic (including electromagnetic) test methods, to test for any one or more of: integrity, lay length, breakage, damage of the rope or its components. A magnetic detection element typically runs longitudinally and may comprise a metal wire or filament consisting of metal. Alternatively, a magnetic detection element may comprise any synthetic material (e.g. as for the other strength member elements of the rope) but which has been treated or modified in some way to enable the element to be detectable by any magnetic test method to obtain for example magnetic flux leakage or eddy current output data.

For example one or more strength member elements may be treated by including an outer coating or cladding, which coating or cladding is detectable by a magnetic test device, for example as disclosed herein. The elements may be synthetic fibres that are coated with any material detectable by magnetic methods such as for example the detectable material may be adhered, coated, clad, dyed, or otherwise attached to the synthetic fibres. The detectable material may be derived from for example a metallic material such as nickel, iron, cobalt, copper or steel. The synthetic fibres may be treated by adding onto the synthetic fibres the coating or cladding material by any suitable method(s) or metal. A treated synthetic fibre may alternatively comprise another magnetically detectable material such as, but not limited to, electro-conductive textiles, where a synthetic fibre is treated by methods such as coating, embedment, or cladding with a material that responds to electro-magnetism.

In other embodiments the elements may comprise optical transmission elements derived from, for example, glass fibres, such as in a fibre optic cable. The optical transmission elements are generally not detectable by magnetic techniques. However, a synthetic fibre or treated glass fibre as described herein may be incorporated with the optical transmission elements, allowing the fibre optic cable to be detectable by magnetic methods as described.

A rope that is suitable for testing with the methods and devices described herein may consist exclusively of magnetic detection elements, or alternatively may include both non-magnetic or "normal" strength member elements and one or more magnetic detection elements. Where both are present, each magnetic detection element may correspond substantially in materials and properties to the normal strength member elements present with the exception of the additional magnetic material present thereon. Similar strength, stiffness and elasticity properties may be desired, especially if the integrity and condition of the magnetic detection element(s) is/are intended to be directly indicative of the condition and integrity of all elements present. On the other hand, under certain circumstances it may be desirable for the magnetic detection element(s) to have different strength, elasticity, stiffness or other physical properties to their regular strength member element counterparts. For example, if the magnetic detection elements are stiffer than their normal counterparts they may tend to be damaged or break more easily, and thus detected by the disclosed methods and devices.

In selected embodiments there is provided an apparatus for measuring lay length of a synthetic rope comprising at least one magnetic detection element that completes one or more circumferential, helical or sinusoidal path(s) around or within the synthetic rope for each lay length of the rope. Specifically the apparatus may comprise:
- a sensor device having a body defining an elongate passageway enabling the synthetic rope to be advanced there through in a direction of the central axis of the rope while permitting limited lateral movements of the rope;
- sensors on the body of the sensor device, sensing changes in magnetic flux in the region of the rope caused by variations in the magnetic flux of the at least one magnetic detection element and/or its proximity and to the sensors, thereby to generate an oscillating pattern of detected magnetic flux as the rope advances through the passageway;
- means for associating the detected oscillations with physical distances along the rope; and
- a lay length calculator or display that calculates or displays a distance along the synthetic rope of one or more of the detected oscillations correlating to the number of circumferential, helical or sinusoidal paths of the magnetic detection element around or within the rope.

In this way, the apparatus uses magnetic flux detection to assess the rope's lay length preferably without affecting, damaging or destroying the rope. Each magnetic detection element may be visible or concealed within the rope, or may be concealed with a sheath or covering of the strength elements of the rope. If more than one magnetic detection element is present for the apparatus to detect then a user of the apparatus may wish to know whether the magnetic detection elements are bound together in the rope, such that a single oscillating pattern of detected magnetic flux is observed by the user. Alternatively, if for example two magnetic detection elements are present in the rope, for example wound helically on opposite sides of the rope, then two oscillating patterns may be detected by the apparatus as the rope advances. Further oscillations may be detected if multiple magnetic detection elements are present in different locations on or within the rope. Such additional oscillations may need to be accounted for, and may indeed assist, in calculation of lay length.

The sensors of the apparatus may be of any type suitable to detect magnetic flux, and sensitive enough to detect magnetic flux of the at least one magnetic detection element, regardless of whether each magnetic detection element comprises at least one metallic fibre or at least one synthetic fibre that has been treated so as to be detectable by the sensors. For example, the sensors may sense changes in magnetic flux of the at least one magnetic detection element, each of which has been pre-conditioned by passing the rope through a magnetic field at least substantially perpendicular to a direction of movement of the rope through the sensor device, prior to being passed through the sensor device. Optionally, the sensor device of the apparatus may further comprise one or more generators of magnetic flux, such as but not limited to permanent magnets, electromagnets or coils, to generate the magnetic field at least substantially perpendicular to the direction of advancement of the rope through the sensor device, thereby to precondition the at least one magnetic detection element of the rope.

In some embodiments of the apparatus, the sensors of the sensor device may be spaced circumferentially around the rope as it is advanced through the passageway, and the signals generated by the sensors optionally subtractively combined to eliminate components due to any lateral movement of the rope. For example, the sensors may optionally be arranged on the sensor device about a common plane transverse to the central axis of the rope. The sensors can even be arranged, if so desired, circumferentially about the passageway equidistant from a central axis of the rope when free of lateral movement in the passageway. Such sensors may be selected from, but are not limited to, Hall Effect devices, flux gate sensors, or induction coils.

For example the sensors may take the form of magnetic induction coils formed of electrical wire wound into coils having a clockwise or anticlockwise winding direction, the winding direction of the coils of a first group of sensors all being the same, and the winding direction of the coils of a second group of sensors all being the same but opposite to that of the sensors of the first group. The electrical coils may all be interconnected in a single circuit functioning, due to said winding directions of the induction coils of the first and second groups, as a circuit for subtractively combining signals, the output of which is a combined signal for calculation of the lay length. The use of sensors comprising magnetic induction coils is particularly useful where the rope advances through the apparatus and past the sensors at relatively high speed.

In further selected embodiments of the apparatus the sensor device may comprise two separable halves surrounding the passageway to enable the sensor device to be installed around the synthetic rope positioned in the passageway. For example, the halves may be temporarily separated, or separated on one side by a hinged movement, so that the rope can be laterally inserted into the passageway, and the two halves hinged back together or otherwise reconnected, thus to capture the rope in the passageway for axial movement therethrough.

Each apparatus may include a sensor device, as already explained, made in two device halves. This design allows the device to be opened and positioned around the rope while the rope is in situ for operational use, for example in a winding apparatus. The two halves may be joined together at one side by one or more hinges and held in place on the other side by releasable latches. The device can be, for example, mounted on a fixed piece of a winding apparatus, e.g. immediately below a winding wheel in the winding shack where rope whipping is usually at a minimum. In order to allow the measurement device to be opened without affecting the coil circuits, the connections between wires of the halves may be positioned close to their connecting hinge and provided in the form of a jumper cable with enough slack to allow the device to be fully opened without causing breakage of the wires. External connection points for the circuits may be located on the side of the device opposite to the hinge near the latch.

In further exemplary embodiments of the apparatus, the sensor device may further comprise one or more generators of magnetic flux positioned to create a magnetic flux circuit having a part thereof passing through a region of the rope when present in the passageway, the sensors sensing magnetic flux leakage from the rope.

Alternatively the sensor device may further comprise means to generate eddy currents in the at least one magnetic detection element, the sensors sensing magnetic fields produced by the eddy currents.

In still further embodiments, the apparatus is also for detecting breakages in one or more of said at least one magnetic detection elements, the apparatus comprising one or more generators of magnetic flux, such as but not limited to, permanent magnets, electromagnetic or coils, to generate a magnetic field at least substantially parallel to the direction of advancement of the rope, to precondition the at least one magnetic detection element so that the sensors sense signals indicative of damage and/or breakages in the magnetic detection elements. As an option, the one or more permanent magnets that generate the magnetic field at least substantially parallel to the direction of advancement of the rope may optionally comprise one or more circular permanent magnets.

In any of the described embodiments the apparatus may further comprise: (1) one or more permanent magnets, electromagnets or coils, to generate a magnetic field at least substantially perpendicular to the direction of advancement of the rope through the sensor device, to precondition the at least one magnetic detection element so that the sensors sense a lay length of the rope; and (2) one or more permanent magnets, electromagnets or coils, to generate a magnetic field at least substantially parallel to the direction of advancement of the rope, to precondition the at least one magnetic detection element so that the sensors sense signals indicative of breakage or damage to the at least one magnetic detection element. For example, in some such embodiments the one or more permanent magnets, electromagnets or coils of a. may be positioned on one side of the sensors such that the at least one magnetic detection element is preconditioned for lay length detection when the rope is advanced a first way though the passageway. The one or more permanent magnets, electromagnets or coils of b. may be positioned on an opposite side of the sensors from those of a. so that the rope is preconditioned for breakage detection when advanced through the passageway in a second direction opposite to the first direction. In such embodiments, electromagnets or coils may be particularly useful as means to precondition the rope because the magnetization direction or orientation may be changed according to the electric current and voltage applied to the electromagnets or coils. In this way, the electromagnets or coils may be induced to generate alternative magnetic fields according to whether preconditioning for lay length detection, or element breakage/damage detection, as required at any given moment.

For certainty, for any of the apparatus embodiments disclosed herein for lay length detection, the apparatuses may also be for testing the synthetic rope for breakage points or damage to the at least one magnetic detection element, wherein the sensors on the body of the sensor device also sense changes in magnetic flux in the region of the rope caused by breakage points or damage to the at least one magnetic detection element. In this way, the calculator or display further calculates or displays recorded data corresponding to the changes in magnetic flux resulting from said breakage points or damage.

In other embodiments, regardless of a lay length of the rope, apparatuses are provided for testing a synthetic rope comprising at least one magnetic detection element running the length of the synthetic rope, the apparatus comprising:

a sensor device having a body defining an elongate passageway enabling the synthetic rope to be advanced there through in a direction of the central axis of the rope while permitting limited lateral movements of the rope;

sensors on the body of the sensor device, sensing changes in magnetic flux in the region of the rope caused by breakage points or damage to the at least one magnetic detection element;

a calculator or display that calculates or displays recorded data corresponding to the changes in magnetic flux; and optionally means for preconditioning the at least one magnetic detection element by generating magnetic flux therein, suitable for damage or breakage detection.

In this way, selected embodiments provide for an apparatuses whose sole or primary function is to detect breakages or damage to one or more magnetic detection elements of a synthetic rope, regardless of the rope's lay length, and regardless of whether or not the magnetic detection elements adopt spiral, helical or sinusoidal paths in the rope.

In still further embodiments there is provides a use of any apparatus disclosed herein, for testing a synthetic rope comprising at least one magnetic detection element, to assess at least one of: the integrity, the strength, the safety, the lifespan, the load capacity, the wear, the lay length, faults or breakages of the at least one magnetic detection element, of the rope or portions thereof. Optionally with respect to such a use, the testing occurs while the rope is in operational use, or without removal of the rope from its point of operational use.

In further embodiments there is provided a method for testing a lay length of a synthetic rope comprising at least one magnetic detection element running through the rope, the method comprising an initial step of: applying any apparatus of as described herein for measuring lay length to the rope, so that the rope passes through the passageway of the sensor device. In another step the rope is advanced through the passageway so that the sensors on the body of the sensor device sense changes in magnetic flux in the region of the rope caused by variations in the proximity and/or magnetic flux of the magnetic detection element to the sensors, thereby to generate an oscillating pattern of detected magnetic flux as the rope advances through the passageway. The detected oscillations can then be associated with physical distances along the rope, and a lay length calculated or displayed according to a distance along the synthetic rope of one or more of the detected oscillations correlating to the number of circumferential, helical or sinusoidal paths of the magnetic detection element around or within the rope.

In some such embodiments the at least one magnetic detection element comprises at least one metallic fibre or at least one synthetic fibre that has been treated so as to be detectable by the sensors. For example, the at least one synthetic fibre may comprise a synthetic material that is coated with a material detectable by the sensors.

Regardless of the nature, construction or materials of the rope or magnetic detection element(s) contained therein, the method may optionally further comprise a step of pre-conditioning the rope by passing the rope through a magnetic field at least substantially perpendicular to a direction of movement of the rope through the sensor device, before the rope is advanced through the passageway of the sensor device. In this way, the magnetic detection element(s) may be magnetized prior to their analysis by the sensors, the sensors detecting residual magnetism or magnetic flux in the magnetic detection element(s) suitable to test for damage to, or breakage of, one of more of the elements. For example, the step of pre-conditioning may be carried out by way of a magnetic field (at least substantially perpendicular to a direction of movement of the rope) generated by one or more permanent magnets, electromagnets or coils.

In certain embodiments the sensors may be spaced circumferentially around the rope as it is advanced through the passageway, and the method may further comprises subtractively combining the signals generated by the sensors to eliminate components due to any lateral movement of the rope. Optionally, the sensors on the sensor device may be arranged on a common plane transverse to the central axis of the rope. Optionally, the sensors may be arranged circumferentially about the passageway equidistant from a central axis of the rope when free of lateral movement in the passageway. Such sensor arrangements are considered, at least in some embodiments, the help optimize signal receipt and analysis.

For any of the methods described, any suitable sensors for magnetism or magnetic flux may be used, including but not limited to: Hall Effect devices, flux gate sensors, or induction coils. The sensors are optionally magnetic induction coils formed of electrical wire wound into coils having a clockwise or anticlockwise winding direction, the winding direction of the coils of a first group of sensors all being the same, and the winding direction of the coils of a second group of sensors all being the same but opposite to that of the sensors of the first group. Such electrical coils can optionally all be interconnected in a single circuit functioning, due to the winding directions of the induction coils of the first and second groups, as a circuit for subtractively combining signals, the output of which is a combined signal for calculation of said lay length.

In any of the methods described, the sensor device may comprise two separable halves surrounding the passageway, the step of applying the apparatus to the rope comprising at least partially separating the separable halves to install the halves about the synthetic rope such that the rope runs through the passageway. Ideally the passageway has a certain size, once the halves are brought together, such that the rope can run in an axial direction through the passageway without significant lateral movement.

Other embodiments of the methods described herein include a further step of creating a magnetic flux circuit having a part thereof passing through a region of the rope when present in the passageway, from one or more generators of magnetic flux, the sensors sensing magnetic flux leakage from the rope, or the at least one magnetic detection element. Alternatively, magnetic analysis may comprise creating eddy currents in the at least one magnetic detection element, the sensors sensing magnetic fields produced by the eddy currents.

Still further embodiments of the methods include assessment of possible damage or breakage of the at least one magnetic detection element. For example, such methods may further comprise generating a magnetic field at least substantially parallel to the direction of advancement of the rope, to precondition the at least one magnetic detection element so that the sensors sense signals indicative of breakages or damage in one or more of the at least one magnetic detection elements. Optionally, the magnetic field at least substantially parallel to the direction of advancement of the rope is generated by one or more permanent magnets, electromagnets or coils, preferably one or more circular permanent magnets.

For example, the methods may further comprise:
generating, with one or more permanent magnets, electromagnets or coils, a magnetic field at least substantially perpendicular to the direction of advancement of the rope through the sensor device, to precondition the at least one magnetic detection element so that the sensors sense a lay length of the rope; and
generating, with one or more permanent magnets, electromagnets or coils, a magnetic field at least substantially parallel to the direction of advancement of the rope, to precondition the at least one magnetic detection element so that the sensors sense signals indicative of said breakages.

Such methods optionally permit the rope to be advanced 'backwards' and 'forwards' in both axial directions to assess both lay length and also damage or breakage of the magnetic detection elements. Optionally, the step of advancing may comprise movement of the rope through the passageway in both axial directions in any order, optionally repeated, the one or more permanent magnets, electromagnets or coils of
a. positioned on one side of the sensors such that the at least one magnetic detection element is preconditioned for lay length detection when the rope is advanced a first way though the passageway, and the one or more permanent magnets, electromagnets or coils of b. are positioned on an opposite side of the sensors from those of a. so that the rope is preconditioned for breakage detection when advanced through the passageway in a second direction opposite to the first direction. In such embodiments, electromagnets or coils may be particularly useful as means to precondition the rope because the magnetization direction and/or orientation may be changed according to the electric current and voltage applied to the electromagnets or coils. In this way, the electromagnets or coils may be induced to generate alternative magnetic fields according to whether preconditioning for lay length detection, or element breakage/damage detection, is required at any given moment.

In certain embodiments, any of the described methods are also for testing the synthetic rope for breakage points or damage to the at least one magnetic detection element, wherein in the step of advancing, the sensors on the body of the sensor device also sense changes in magnetic flux in the region of the rope caused by breakage points or damage to the at least one magnetic detection element. In the step of calculating or displaying, the calculator or display further calculates or displays recorded data corresponding to the changes in magnetic flux resulting from the breakage points or damage of the magnetic detection elements.

In any of the methods described here, the synthetic rope may be selected from synthetic rope, synthetic yarn, synthetic cord, a fibre optic cable, Any of the methods described may further comprise a preliminary step of: providing a synthetic rope comprising synthetic material strength member elements, wherein at least one element is a treated element to form a magnetic detection element suitable to render the rope capable of being inspected by an apparatus as described herein. Alternatively, any of the methods described may further comprise a preliminary step of: providing a synthetic rope comprising synthetic material strength member elements, and at least one metal fibre to form a magnetic detection element suitable to render the rope capable of being inspected by an apparatus as described herein.

In a still further embodiment there is provided a method for testing a synthetic rope comprising at least one magnetic detection element running the length of the synthetic rope, the method comprising the steps of: applying to the rope an apparatus as described for assessing possible breakage and/or damage to magnetic detection elements, such that the rope passes through the elongate passageway; advancing the rope through the passageway, the sensors sensing changes in magnetic flux in the region of the rope caused by breakage points or damage to the at least one magnetic detection element; and calculating or displaying data corresponding to the changes in magnetic flux indicative of said breakages or damage to the at least one magnetic detection element.

Figure 2:
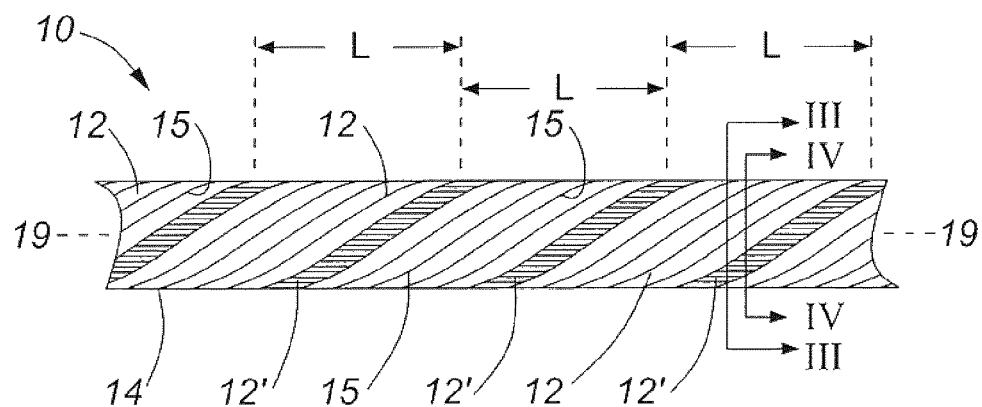
FIG. 2 illustrates a side view of an example rope comprising magnetic detection elements that may be observed on an exterior of the rope as shown. Although the basic construction of the rope illustrated is typical of a wire rope, the principles regarding lay length and the presence of a magnetic detection element nonetheless apply to synthetic ropes. The embodiment illustrated is exemplary, and in other embodiments the presence of one or more magnetic detection element may be masked by an additional cover or coating on the rope, or the magnetic detection element(s) may be concealed within a structure of the rope, for example by being woven into the rope without any portion exposed upon the rope exterior.

FIGS. 1 and 2 of the accompanying drawings show a cross-section of one form of rope 10 having a core strand 11 covered by six spirally wound outer strands 12 typically used for mining operations, although it should be kept in mind that ropes of other designs may alternatively be employed, e.g. those having more or fewer external strands, more or fewer core strands 11, and strands of non-circular cross-section. It should also be noted that the rope illustrated in FIG. 1 (and indeed FIG. 2 discussed below) has a configuration and structure that is in fact typical of a wire rope. Nonetheless, for the sake of the present discussion with regard to synthetic ropes, the same principles apply with regard to lay length and fault detection and the presence of multiple strength elements, only some of which are magnetic detection elements as described below.

The core strand 11 and the external strands 12 are each made up of bundles of individual strength member elements 13 (i.e. synthetic or non-metallic elements for synthetic rope construction) twisted or bundled together. In this example, one of the external strands 12 includes three elements 12' that have been pre-treated before manufacture of the rope to provide magnetic detection elements. As best seen in FIG. 2, the magnetic detection elements 12' are visible on the outer surface 14 of the rope, and the rope also includes the external strands 12 separated by grooves 15 between the strands, thereby causing the rope to have a spirally grooved outer surface. Each of the external strands 12 twists around the rope in spiral loops separated from each other along the rope by the five other strands 12. The lay length of such a rope is the distance L along the axis or centerline of the rope required for a single strand to complete a single full circumferential spiral path around the core of the rope, i.e. to progress around the rope and return to the same angular position at the circumference of the rope. A conventional way of measuring the lay length would be to measure a number of such distances (e.g. the three shown in FIG. 2) using a ruler or similar measuring device, and then to calculate the average of such measurements (dividing by three in the case of FIG. 2).

Although in FIG. 2 the magnetic detection elements 12' happen to be visible, in other embodiments the magnetic detection elements may not be visible on an exterior surface of the rope as the rope may include a sheath or coating, or alternative the magnetic detection elements maybe positioned internally for example as inner elements of external strands 12 or as part of internal strand 11.

In the embodiment illustrated, the magnetic detection elements themselves spiral about the outer surface of the rope. Therefore, as the rope advances longitudinally (i.e. along central axis 19) past fixed points of observation the presence of a magnetic detection element 12' may be detected by a device as described herein, and the distance between the sensed magnetic detection elements measured in physical terms, thus permitting measurement of lay length L. For example, residual magnetic flux present in the magnetic detection elements may be sensed by magnetic flux sensors positioned at such points of observation which would, if sufficiently accurate, record undulating sinusoidal-like variations in magnetic flux as the rope advances longitudinally (and without rotation) along its central axis. Such sinusoidal variations can thus be used to measure the lay length of the rope. For example, a measurement of this kind would provide an oscillating generally sinusoidal output as the rope advances, with the distance of rope advancement causing a single oscillation representing one lay length of the rope in the example presented. Any such oscillations along the rope would reveal the lay length at the corresponding positions along the rope, thus showing local lay length measurements, or alternatively, more oscillations over a longer section of the rope (or the entire rope) could be used to provide an average lay length value for that section or for the entire rope.

To associate the oscillations with distances along the rope, means to measure distances of the rope paid out, or means to relate times of measurements to speed of rope advancement, may be employed. However, means for recording rope advancement speed and/or distance are normally provided in equipment used for controlling mine hoisting systems or similar apparatus. For example, rope is often paid out by passing it around a rotating winding wheel, the speed of rotation or number of revolutions of which can be determined conventionally, so that paid-out distances and speeds can be accurately calculated.

Nevertheless, practical difficulties are encountered if attempts are made to use such magnetic flux oscillations to calculate lay length. For example, a rope tends to move laterally (off-axis) by considerable amounts as it advances longitudinally, e.g. ropes tend to whip from side to side or to move off-axis due to harmonic lateral oscillations, so the surface of the rope will move towards and away from a fixed point of observation for this reason. Such off-axis movements can thus present problems to rope analysis.

In one exemplary embodiment, these problems associated with lay length measurement are at least partially addressed by providing sensors in at least two fixed positions spaced angularly around the rope. The fixed positions, and sensors located at such positions, generally all lie in the same plane transverse to the axis of the rope at the same radial distance from the rope axis (when the rope is free of lateral movement), and are located such that one position (or one group of positions) faces one side of the rope surface when another position (or another group of positions) faces an opposite side of the rope surface. Magnetic flux measurements at the two positions (or groups of positions) are generally affected in the same way and at the same time by off-axis movements of the rope. If the two sensors located at the fixed positions are close together, they are affected in the same way by off-axis movements of the rope, so the signals from the sensors can simply be subtracted from each other to reveal the oscillating pattern caused by the measured changes in magnetic flux resulting from changes in the proximity and/magnetic flux of the at least one magnetic detection element from the sensors. In other words, the signals are subtractively combined, i.e. combined in such a way that one signal is made positive and the other signal negative as they are combined together.

In one practical embodiment, a plurality of sensors are provided and arranged at fixed positions angularly spaced around the rope with the sensors interconnected to form two groups of sensors. The sensors of the two groups are normally alternated in position around the rope, i.e. each sensor of the first group is positioned between two sensors of the second group, and vice versa. The signals from the sensors of the first group are additively combined (combined in a positive sense) and signals from sensors of the second group are additively combined to form two signals that are then subtractively combined. The additive combination of signals reinforces or amplifies the signals of each group and makes the desired components of the signals easier to differentiate from background noise. Lateral movements of the rope affect the signals from each of the two groups of sensors in essentially the same way due to the even spacing of the sensors around the wire rope so that the subtractive combination of the signals from the two groups effectively cancels this component.

The subtractive combination of the signals may be effected by suitable means, e.g. a programmable logic controller, computer or similar calculator, or alternatively, the sensors may all be connected together in a single circuit, but with alternate sets of sensors arranged to generated signals having opposite senses (one set produces a positive signal when the other produces a negative signal) thereby generating a common signal from which the off-axis components have been automatically deleted before delivery of the signal to monitoring apparatus. Such an arrangement combines the functions of additive combination of signals from sensors of the same group and subtractive combination of the signals from the different groups.

To measure variations of magnetic flux, it is possible to employ sensors that measure magnetic flux, such as Hall Effect sensors and flux gate sensors. These are known devices previously used to measure the metallic area of a wire rope (Hall Effect sensors) or wire rope defects (flux gate sensors). Again, a plurality of such sensors is arranged around the rope and signals from two such sensors (or two groups of such sensors) are subtracted to reveal the generally sinusoidal oscillation caused by the magnetic flux of the magnetic detection element in the rope while eliminating signals caused by lateral (off-axis) movement of the rope.

Thus, in certain embodiments the rope comprising one or more magnetic detection elements may be 'conditioned' by passing the rope through a magnetic field oriented in the direction in which measurement is contemplated: e.g. a field that is at least substantially parallel to an axial direction of movement of the rope through the apparatus to detect damage or breakage to the magnetic detection elements, and/or a field that is at least substantially perpendicular to an axial direction of movement of the rope through the apparatus to detect lay length. Optionally, the 'conditioning' may be achieved using appropriately positioned and oriented permanent magnets, electromagnets or coils.

Once 'conditioned' (if necessary and required) the rope then passes in between a pair of sensors that are suitably sensitive to obtain a signal corresponding to the detection of the residual magnetic field from the conditioned/magnetized magnetic detection element. Ideally, though not necessarily, the magnetic detection element comprises a material with a high degree of remanence to retain a degree of magnetism even after a magnetic field is removed once the material has been 'conditioned'. As described in more detail herein, lay length may be calculated from the oscillating signals obtained by the sensors, whereas alternatively or additionally any damage and/or breakage of the magnetic detection elements may be determined by disruptions or variations in the signals obtained by the sensors.

In select embodiments it is even possible to use the same pair of sensors to detect breakages and to measure lay length. To achieve that, the 'conditioning' units such as permanent magnets, electromagnets or coils can optionally be positioned on each side of the pair of sensors relative to the axis and direction of movement of the rope. For example, permanent magnets to condition the rope for lay length measurement may be positioned on one side of the sensors, the rope being conditioned for lay length measurement before advancing axially in close proximity to the sensors. Additional permanent magnets for breakage or damage detection may be positioned on an opposite side of the sensors compared to the permanent magnets for lay length detection, such that when the direction of axial advancement of the rope is reversed the rope is alternatively 'conditioned' by the additional permanent magnets before advancing axially in close proximity to the sensors.

Figure 3:
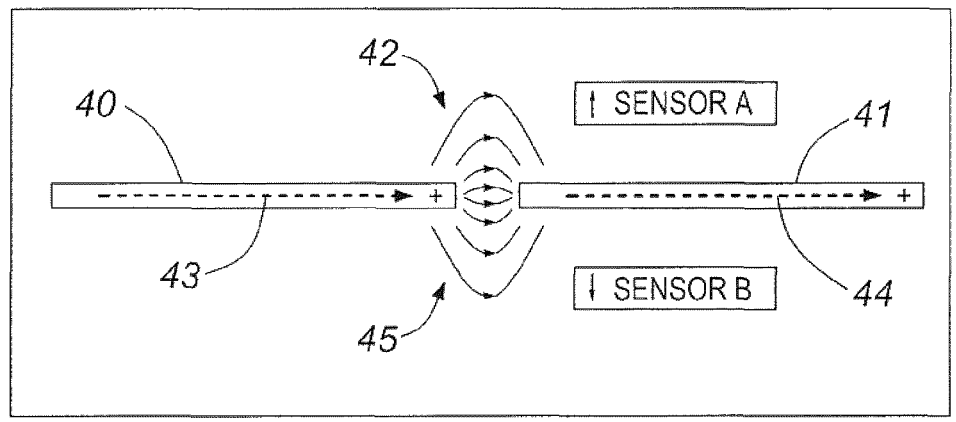
FIG. 3 illustrates magnetic flux detection at a point of breakage in a magnetic detection element.
Figure 4:
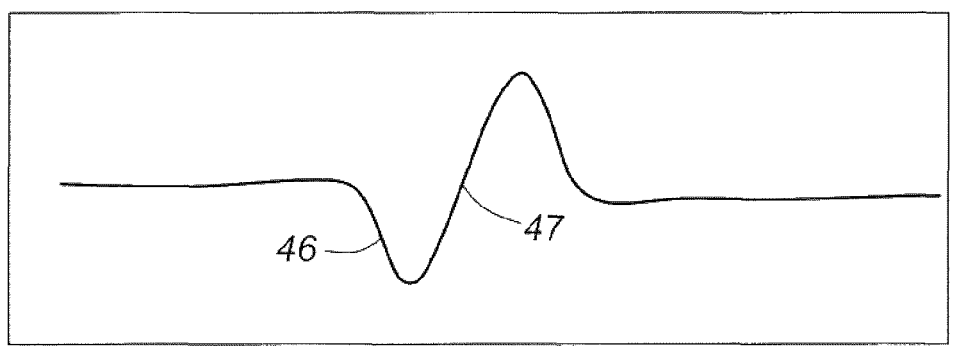
FIG. 4 illustrates schematically a typical magnetic flux reading as the magnetic detection element shown in FIG. 3 passes near or between magnetic flux sensors.

With reference to FIG. 3, to detect breakages or damage to the magnetic detection elements in the rope, permanent magnets, electromagnets or coils, such as but not limited to circular permanent magnets, are arranged so as to produce a pre-conditioning field to magnetize the rope, and specifically the magnetic detection element(s) in the rope. FIG. 3 shows one such magnetic detection element with sections 40, 41 separated by breakage point 45. Due to residual magnetism in the magnetic detection element 40, 41 the breakage results in a residual magnetic field 42 at or near the breakage point 45. By advancing the rope axially in a direction of arrows 43, 44, the rope subsequently advances between sensors A and B, on which are shown directions of measurement. Sensors A and B sense the presence of residual magnetic field 42, and thus produce signals indicative of the residual magnetic field 42. Therefore, signals produced by the sensors A and B may be added (e.g. mathematically and/or electronically) to provide a detection signal for the breakage point 45 which, as shown schematically in FIG. 4, may be observed as a drop 46 followed by an increase 47 in detected magnetic flux.

Figure 5:
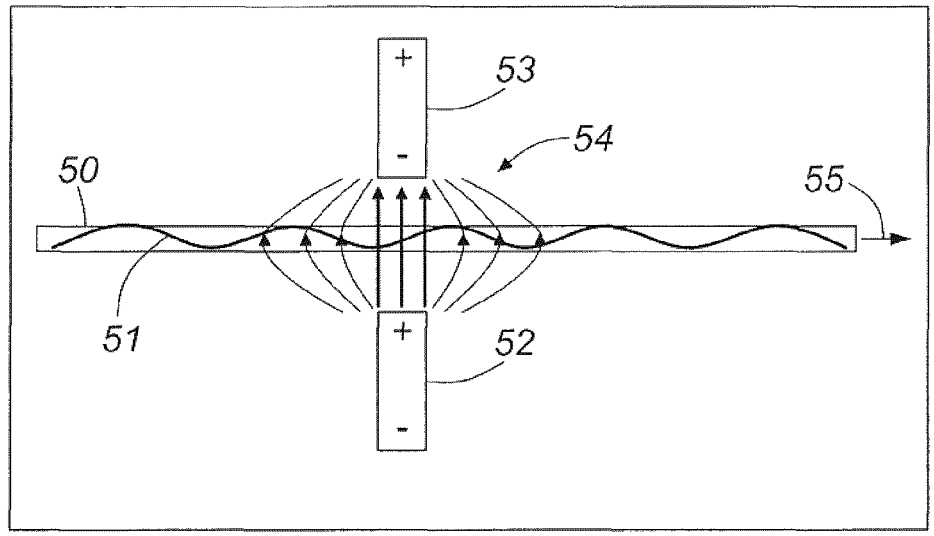
FIG. 5 illustrates preconditioning of a rope comprising a magnetic detection element for lay length analysis using permanent magnets.

FIG. 5 shows schematically conditioning of a rope for lay length detection. In this example, the rope 50 comprises a magnetic detection element 51 that adopts a spiral path through the rope due to the rope's construction, and the twisting or weaving of the other elements present. Permanent magnets 52, 53 generate field 54 that is at least substantially perpendicular to the rope and its direction of axial movement as the rope passes between the permanent magnets 52, 53 in the direction indicated by arrow 55.

Figure 6:
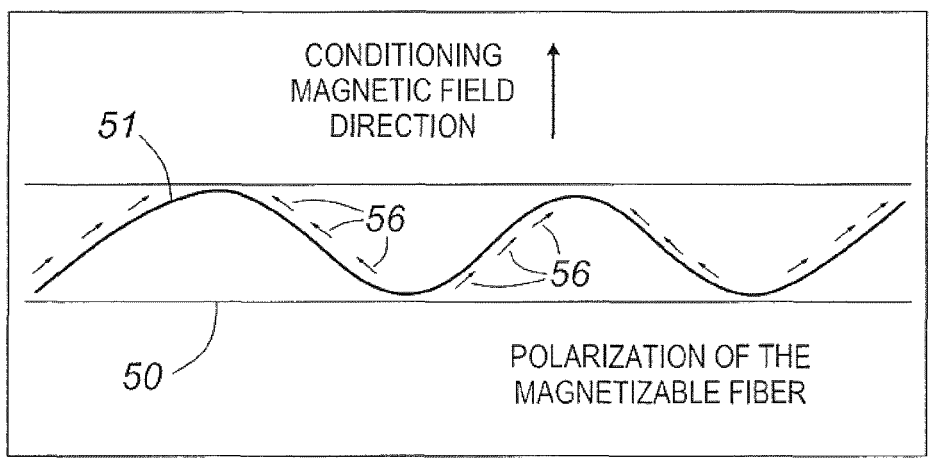
FIG. 6 illustrates schematically polarization upon or resulting from preconditioning in a magnetic detection element of the rope illustrated in FIG. 5.

Therefore, when the rope 50 is advanced axially though field 54 in the direction 55 the magnetic detection element 51 becomes polarized according to its angle relative to the magnetic field 54, in the manner shown in FIG. 6 as shown by polarization arrows 56.

Figure 7:
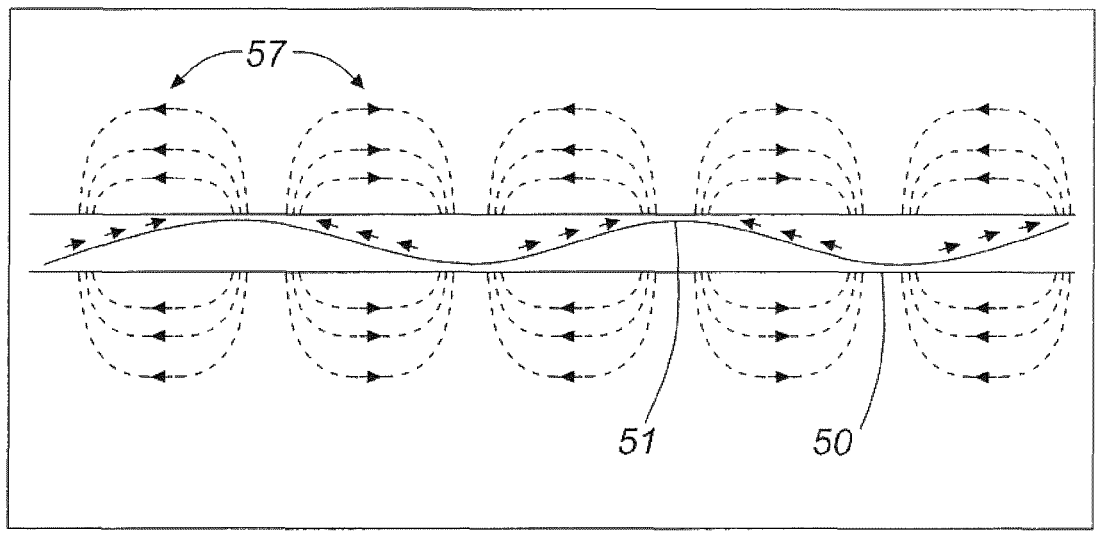
FIG. 7 illustrates residual magnetic flux in the magnetic detection element of the rope illustrated in FIG. 5.

When the conditioning magnetic field 54 is withdrawn, for example by removal of the permanent magnets 52, 53 or by advancement of the rope 50 away from the permanent magnets 52, 53, the residual magnetism in the magnetic detection element 51 generates flux leakages 57 as shown in FIG. 7. Subsequent advancement of rope 50 near or between appropriately positioned sensors (not shown) results in detection of flux leakages 57 to produce a sinusoidal signal, with each complete oscillation of the signal indicative of lay length of the rope providing the distance of advancement of the rope between the oscillations is known (optionally the distance may be calculated based upon knowledge of the speed of rope advancement, and the time between the oscillations).

If multiple magnetic detection elements are present in the rope, they may be bundled together to generate a stronger signal resulting from additive signals from each element in the bundle. If multiple magnetic detection elements are present, which adopt spiral paths axially offset from one another in the rope, additional signal analysis may be required to determine which signal peaks correspond to signals from individual magnetic detection elements.

Although any type of magnetism or magnetic flux sensors may be used, Applicant has developed devices using sensors of the SpinTJ™ type manufactured by MicroMagnetics. Such sensors, or similar other sensors that are available, are useful as they permit measurement of low intensity magnetic fields (e.g. +/−20 Gauss) with a high degree of resolution (e.g. approximately $1/10,000$ Gauss). More specifically, STJ-240 sensors have been used, which act like a variable resistor with a value that correlates to the magnetic field to which they are exposed.

Figure 8:
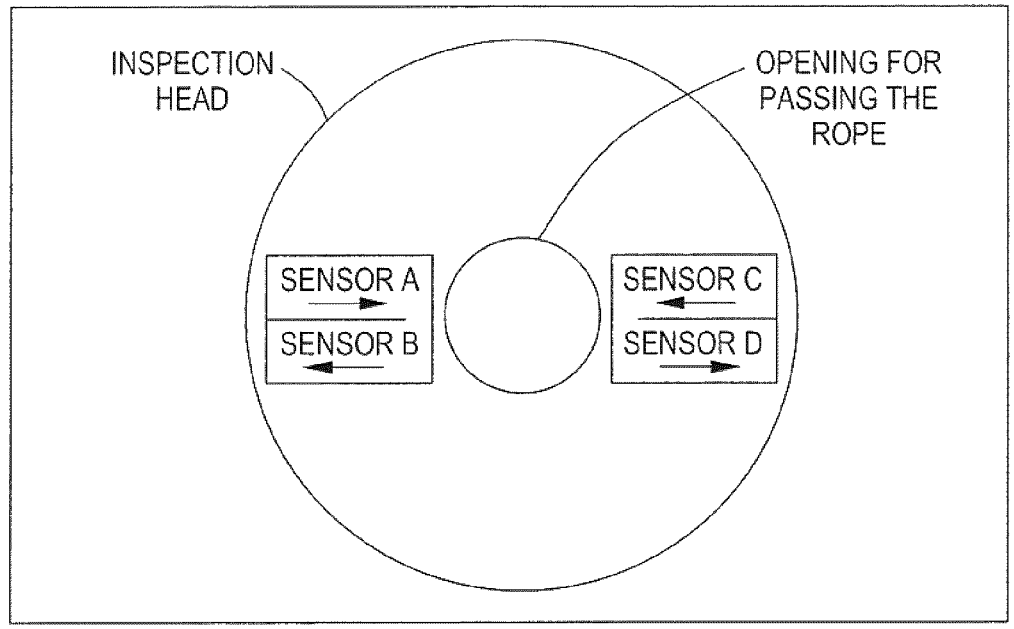
FIG. 8 illustrates schematically an inspection head or sensor device for analyzing a rope comprising a magnetic detection element.
Figure 9:
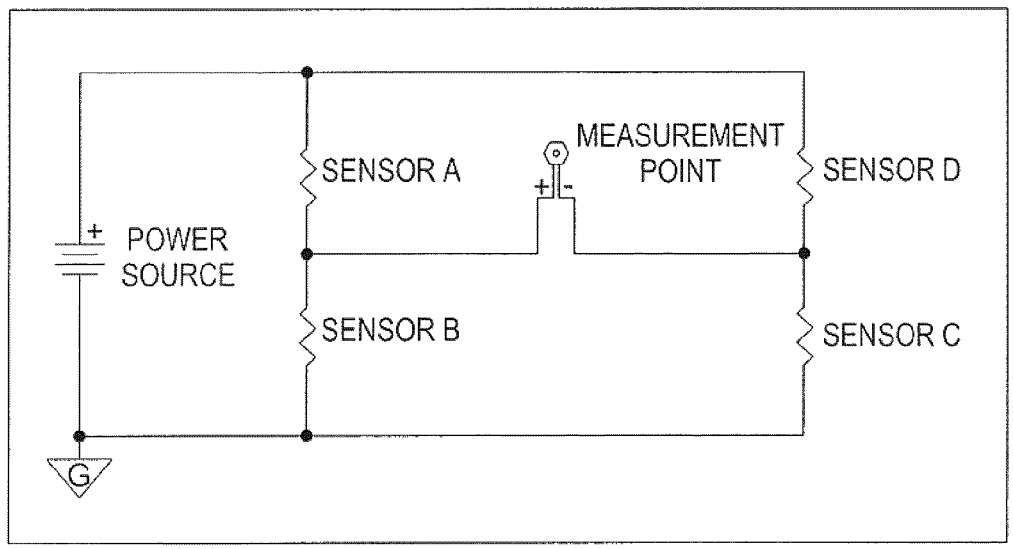
FIG. 9 illustrates schematically a sample circuit diagram (Wheatstone bridge arrangement) suitable for a sensor device or apparatus as disclosed.

Many sensor configurations and component wiring configurations are possible to achieve the apparatuses and methods disclosed herein. One example configuration, which demonstrated useful signal to noise ratios, is a Wheatstone bridge configuration using four sensors. Compared to a commonly used configuration comprising two opposed sensors, the Wheatstone bridge configuration with four sensors permits doubles the sensitivity of the apparatus, whilst inherently suppressing the noise from the power source. FIG. 8 shows an example layout and measurement direction of the sensors, whereas FIG. 9 illustrates an example connection scheme for the apparatus components. In this example, it will be noted that the two sensors of each pair of sensors are mounted in opposite directions compared to the measurement direction.

Figure 10:
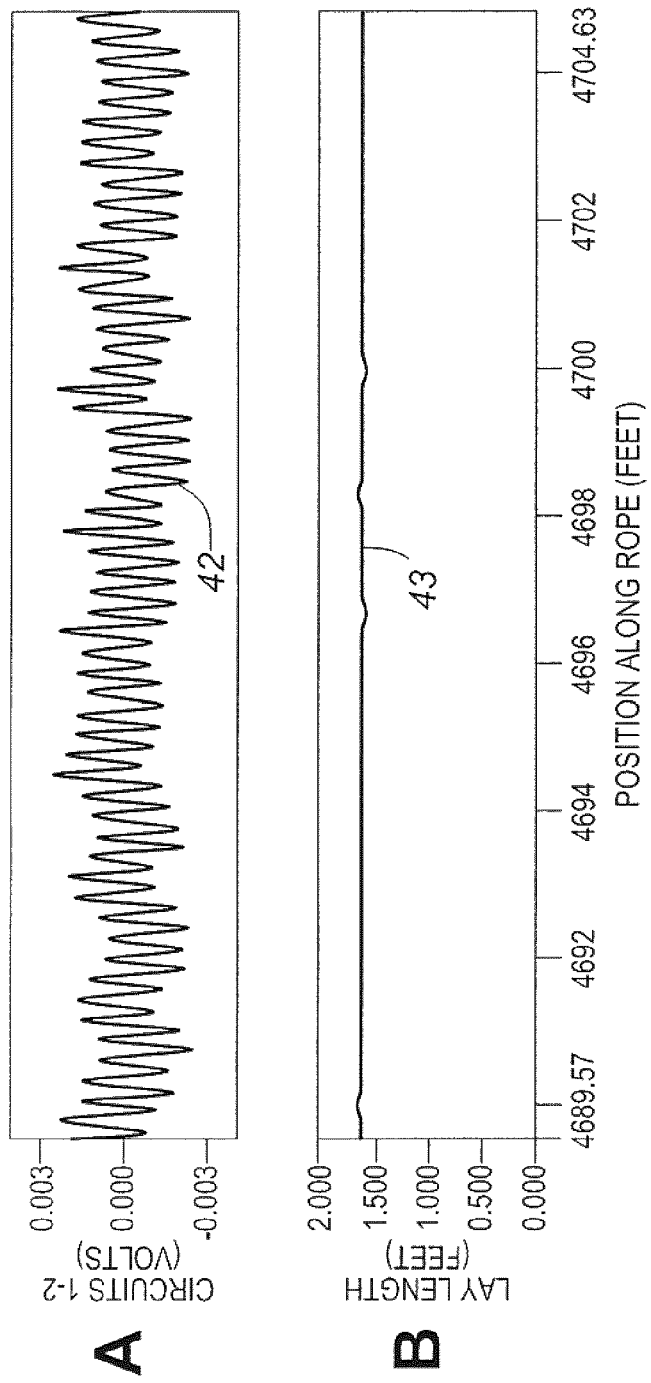
FIG. 10 illustrates schematically sample detection over time of (A) magnetic flux and (B) lay length of a rope comprising a magnetic detection element.

FIGS. 10A and 10B show typical induction signal outputs from a typical apparatus, and thus the lay length of the rope. The plots show signal electrical voltage against distance along the rope (measured by rope speed or distance in meters, not shown). For lay length, and detection of magnetic flux of a magnetic detection element, the result is a sinusoidal-like signal 42 as shown in FIG. 10A. The peaks and troughs along this trace represent the proximity of the sensors of a single magnetic detection element. Assuming the rope is known to have one spiral of magnetic detection element per lay length of rope, and then each oscillation therefore represents one lay length of the rope passing through the measurement device (two or more spirals per lay length are also possible, depending upon rope manufacture, and lay length may be calculated accordingly). The position of such a part of the rope, or its speed of advance, is generally known from the winding apparatus used for paying out the rope, and this can be used to reveal the lay length of the rope at that position. The calculation of lay length obtained in this way can be carried out automatically and continuously by a suitable circuit device, e.g. by a programmable logic controller or the like, to generate a chart such as the one shown in FIG. 10B where the vertical axis represents lay length and the horizontal axis represents distance along the rope. The plot 63 shows the calculated lay length at positions along the rope. Hence, any changes in lay length become clearly apparent and the sections of the rope exhibiting such changes are revealed from the plots. Incidentally, such lay length profiles of a rope generated at different times and stored in memory may subsequently be superimposed on each other to reveal changes of lay length over time.

Figure 11:
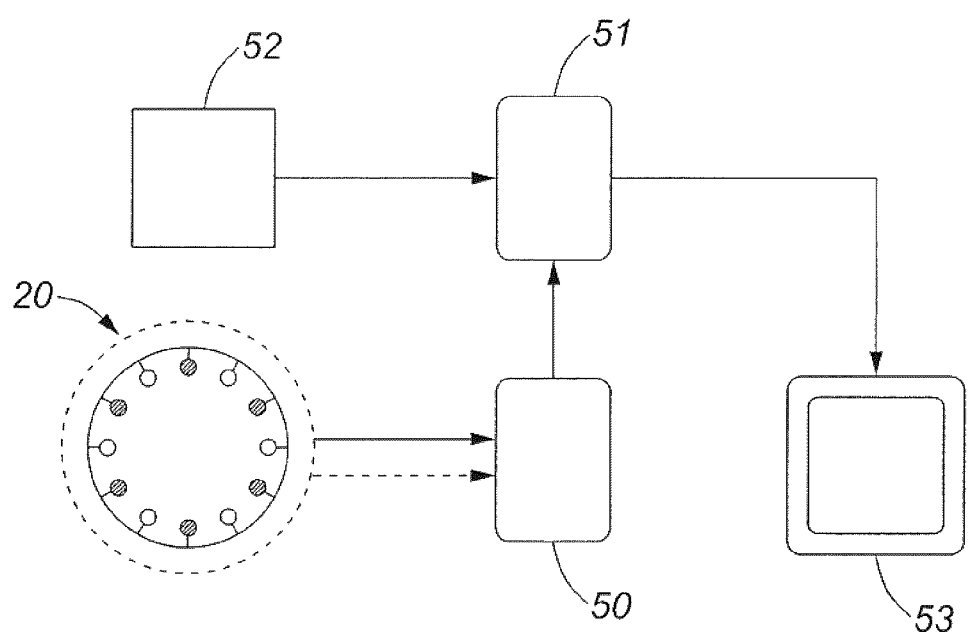
FIG. 11 illustrates schematically an example apparatus setup for testing a rope comprising a magnetic detection element.

FIG. 11 of the accompanying drawings shows in schematic form how parts of the apparatus may be interconnected in one exemplary embodiment of the invention. The signals from the two groups of sensors in the sensor device 20 feed to a circuit 50 for subtractively combining the signals to eliminate components due to transverse movements of the rope (not shown in this figure) and a combined signal is generated and forwarded to a further circuit 51. A device 52 measures distances of rope paid out and fed through the sensor device 20, and a corresponding signal is fed to circuit 51 so that the combined signal from circuit 50 is associated with distances along the rope. The signals so associated are fed to a calculator and display element 53 to calculate lay length of the rope at positions there along and to display the result. The result may also be recorded in this or a separate unit for replay and analysis. In embodiments where the sensors are electrical induction coils with alternating sensors wired in opposite senses and all connected together, the circuit 50 may be eliminated because the wiring of the sensors creates a combined signal from which components due to transverse motion of the rope have been eliminated.

While the sensor device as described includes circuitry for subtracting the signals and calculating or displaying lay length of the rope, the sensor body itself may be provided as a separate component of the apparatus. The body may include the generators of magnetic flux and supporting apparatus, the sensors arranged around the central passageway, and optionally wiring for interconnecting the sensors to form two groups of sensors either having separate signal outputs, or a single combined output if the sensors are of a kind that generate signals of opposite sense.

Figure 12A:
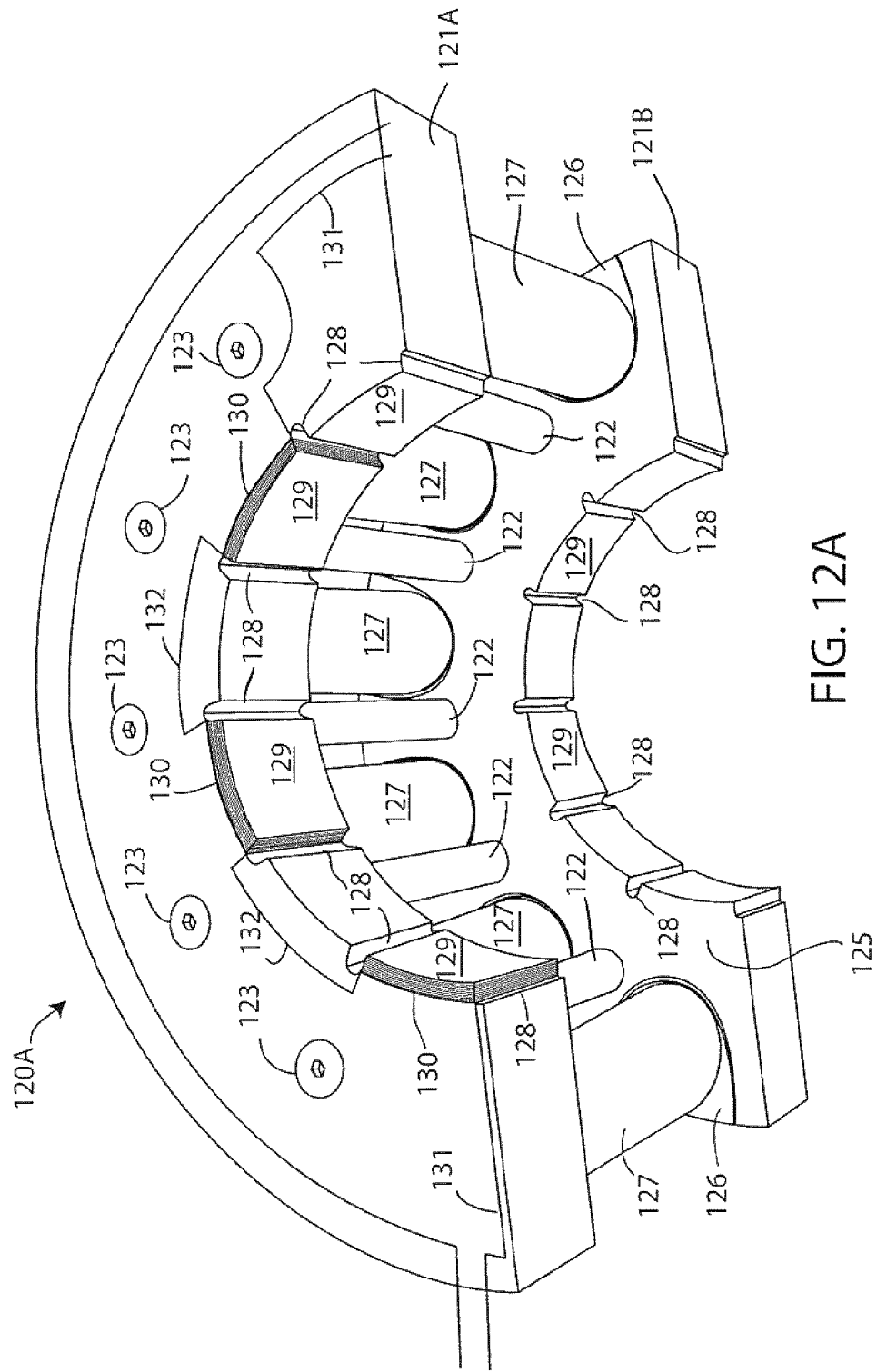
FIG. 12A is a perspective view of a half of a measuring device used for lay length measurement or detection element breakage, the half being an intermediate stage of manufacture.
Figure 12B:
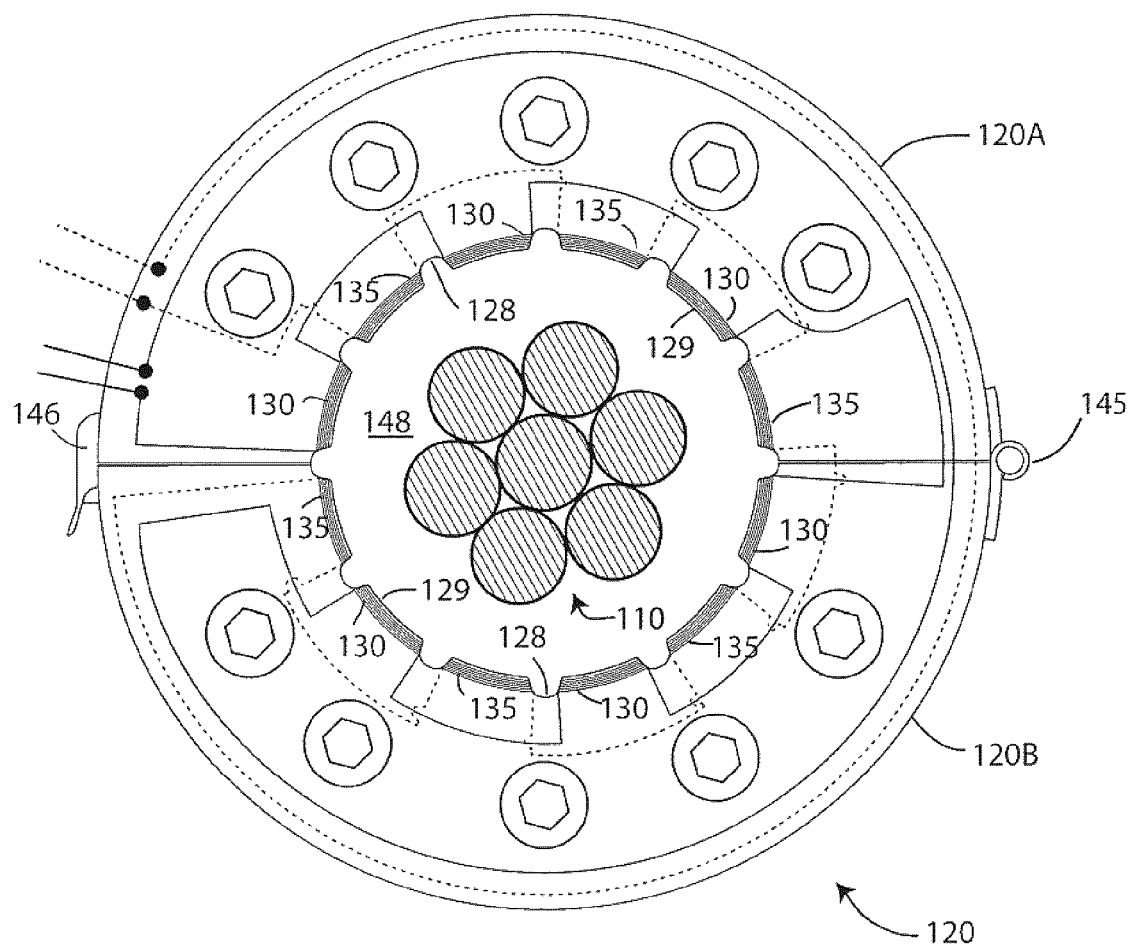
FIG. 12B is a plan view of a completed measuring device made up of two halves, each being similar to the half shown in FIG. 12A.

One exemplary embodiment of apparatus for measuring lay length of a synthetic rope (comprising one or more detection elements) is shown in FIGS. 12a and 12b of the accompanying drawings. The embodiment illustrated, and its features, are merely exemplary and do not limit other embodiments contemplated. FIG. 12A illustrates one half 120A of a sensor device 120 shown at an intermediate stage of manufacture, and FIG. 12B illustrates a plan view of an assembled sensor device 120, made of two halves 121A and 121B positioned together and surrounding a synthetic rope 110. It will be seen from FIG. 12b in particular that the sensor device 120 defines a central elongated passageway through which a synthetic rope 120 may advance in the axial direction of the rope with the possibility of lateral (off-axis) movements.

As illustrated in FIG. 12A, the half 120A of the sensor device 120 forms a body supporting two pole pieces 121A and 121B, made for example of steel, separated from each other and fixed in place by rod-like supports 122 attached by screws 123. The upper surface 125 of the lower pole piece 121B has six semi-elliptical depressions 126 extending inwardly from an outer edge, and the lower surface (not visible) of the upper pole piece 121A has similar semi-elliptical depressions aligned with those below. These depressions may guide and position six optional cylindrical permanent magnets (not visible) held within external mounting tubes 127 so that the ends of the magnets directly contact the pole pieces 121A and 121B. The components of the sensor device other than the optional magnets and pole pieces are preferably made of non-magnetic material such as aluminum.

Figure 13:
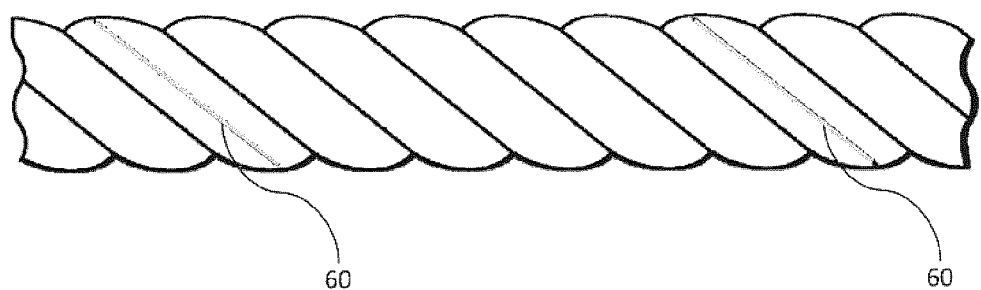
FIG. 13: Example of 6-strand rope with one bundle of marked yarns

In the illustrated embodiment, the Inside surfaces of the pole pieces 121A, 121B are provided with short radial grooves 128. The parts of the pole pieces between these grooves in effect form inwardly facing gear-like projections 129. In the upper pole piece 121A, the projections 129 are wound with copper wire to form magnetic induction sensing coils 130. Only three such coils 130 are shown in FIG. 12A and these are formed on alternate projections 129 (thus, if the projections are numbered consecutively 1, 2, 3, 4, 5 and 6 around the central passageway, only the odd projections 1, 3 and 5 are provided with coils at this stage). These coils are joined together by wires 132 to form a common circuit. At the next stage of production of the sensor device half 121A, coils 135 (see FIG. 13) are provided on the remaining three projections 129 (i.e. the even projections 2, 4 and 6), with such coils being electrically interconnected to form a common circuit, but a circuit separate from that formed by the coils already installed on the odd projections. In the assembled sensor device shown in FIG. 12B, coils 130 and 135 surround the rope 110 and are connected to form two separate electrical circuits (one formed by the "odd" coils 130 and the other formed by the "even" coils 135). A similar half 120B of the sensor device 120 is wired in an equivalent way and the two halves are assembled to produce a cylindrical sensor device 120 as shown in FIG. 12B. In this figure, the wire circuit joining the odd coils is shown in solid lines whereas the wire circuit joining the even coils is shown in dashed lines so that the circuits can be easily distinguished. For the illustrated rope 110, the sensor device has twelve induction coil sensors 130, 135. Other sensor configurations and types may be used as required by the application of the device, or the nature of the rope to be detected.

The coils 130, 135 act as induction coils that generate electrical voltages and/or currents when cut through by moving electrical fields from the flux (e.g. residual magnetic flux) of the at least one detection element. The magnetic flux passing through the region of the rope 110 within the sensor device 120 creates a generally tubular magnetic field through and around the rope (or at least by the detection elements of the rope) and, as the elements of the rope approach or recede from a coil (due to the position of the detection element(s) on or within the rope, and off-axis movement of the rope through the measurement device), varying electric voltages or currents are induced in the coils.

The electrical signals produced by selected coils of the solid line circuit may reinforce each other to produce a stronger signal output depending upon the presence and positioning of one or more detection elements. Likewise the electrical signals of the coils of the solid line circuit may reinforce each other and produce a stronger signal output depending upon the presence and positioning of one or more detection elements. Electrical induction caused by lateral off-axis movement, such as rope whipping, may affect each circuit at the same time and in the same way. The changes in the output signals of the two circuits produced by whipping or other lateral movements are thus similar in the outputs of the two circuits and can be subtracted and the remaining signals combined to reveal the underlying oscillating generally sinusoidal pattern produced by the helical or spiral configuration of the detection element(s) on or within the synthetic rope.

For clarity, it may be noted that the sensors used to sense magnetic flux for the apparatuses described herein are preferably suitable for detection of residual magnetic flux, as expected from one or more detection elements present in the synthetic rope. For example, at least in selected embodiments, the sensors may be sufficiently sensitive to sense changes in the detected magnetic flux in the order of just a few Gauss, or less than one Gauss.

The following examples further illustrate selected exemplary embodiments, and provide corresponding test data. However, such embodiments are in no way intended to limit the scope of the invention or inventions herein disclosed and claimed.

EXAMPLE 1

Non-Destructive Test Methods for High-Performance Synthetic Rope

Interest in high performance-synthetic ropes for mine hoisting has increased as mine operators pursue resources at greater depths. One limiting factor for hoisting capacity is the self-weight of steel wire used as the hoist rope. The significantly higher strength to weight ratio of synthetic rope offers the attractive alternative to enable hoisting a larger payload with a similar size rope and hoisting plant.

Due to the critical nature of hoist rope service, frequent and reliable inspection methods are required and regulated. Visual inspection and a variety of electromagnetic methods are used to monitor in-situ the integrity of presently used wire ropes for mine hoisting. Wire ropes have been used for decades in hoisting applications and the data acquired through nondestructive test (NDT) methods can be correlated with a wealth of data and experience to ensure safe and successful operation.

For synthetic ropes to be used in a hoisting application a multi-faceted approach is proposed to ensure the internal and external integrity of the rope. Visual observations made directly by trained inspectors or with cameras and image processing can thoroughly document the external appearance of the rope and any changes that occur.

This example includes two methods to monitor the internal structure of synthetic hoist ropes in service. Marked yarn magnetic principle based and x-ray inspection methods are introduced with cyclic bending test data to demonstrate an ability to detect internal degradation. Either or both methods could be employed in conjunction with visual inspection techniques to provide the real-time data necessary to safely utilize synthetic ropes in critical applications.

Marked Yarn Magnetic Principle Based Detection:

For the purpose of this discussion, the strength member material of the high performance synthetic rope is aramid. The basic rope structure is 6-strand wire-lay. The aramid rope structure is covered with a braided polyester jacket, obscuring the strength member material from visual inspection.

A small sub-population of strength member material is treated with a marker material that can be monitored by the two methods here discussed. The entire population of treated yarns are bunched together for ease of detection, as shown as a grey line 60 in FIG. 13. One bundle of treated yarns proved adequate for this very simple rope structure. Bundles in multiple locations may be needed for more complicated rope structures.

Figure 14:
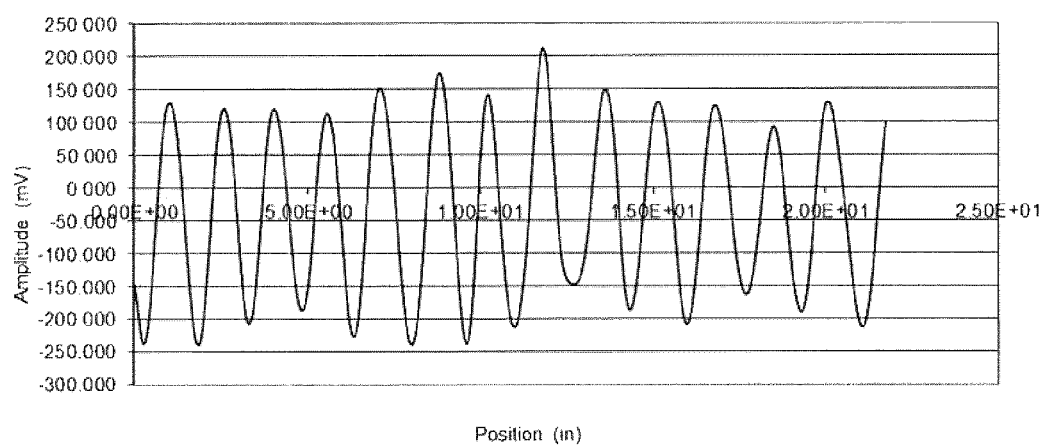
FIG. 14: Sensor output in Location Detection Mode

Data Collection:

A rope in field service can be passed through a detection device that operates in two modes. In the first inspection mode, the location of the treated yarn in the structure can be detected. An example of Location Detection Mode (LDM) output is shown in FIG. 14.

Figure 15:
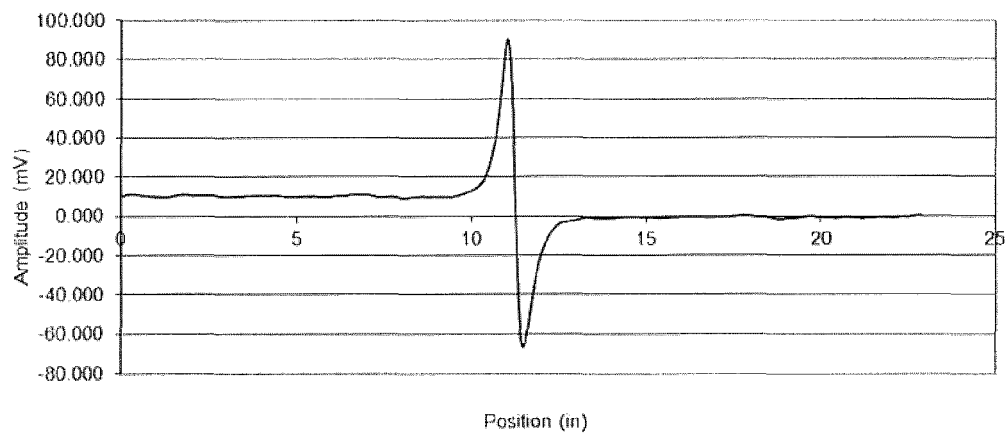
FIG. 15: Sensor output in Breakage Detection Mode

The device can also be configured to detect breakages in the treated yarn, called Breakage Detection Mode (BDM). Output of a breakage sensed in BDM is shown in FIG. 15.

Figure 16:
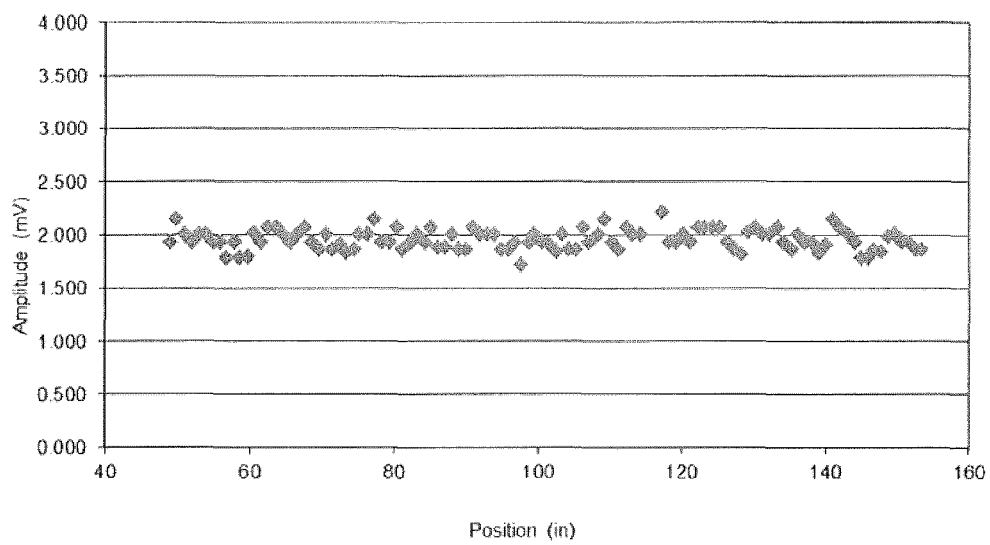
FIG. 16: Lay Length as a function of position

Data Analysis Methods:

The data collected in Location Detection Mode can be used in several ways to determine the Internal condition of the rope. The amplitude of the output data is analogous to the diameter of the rope structure. The period of the output is analogous to the lay length of the rope. Measurements from peak-to-peak of the output data provide localized lay length data, as shown in FIG. 16. A dramatic change in peak-to-peak measurements at any location along the rope would indicate that external damage had been sustained at that location.

Figure 17:
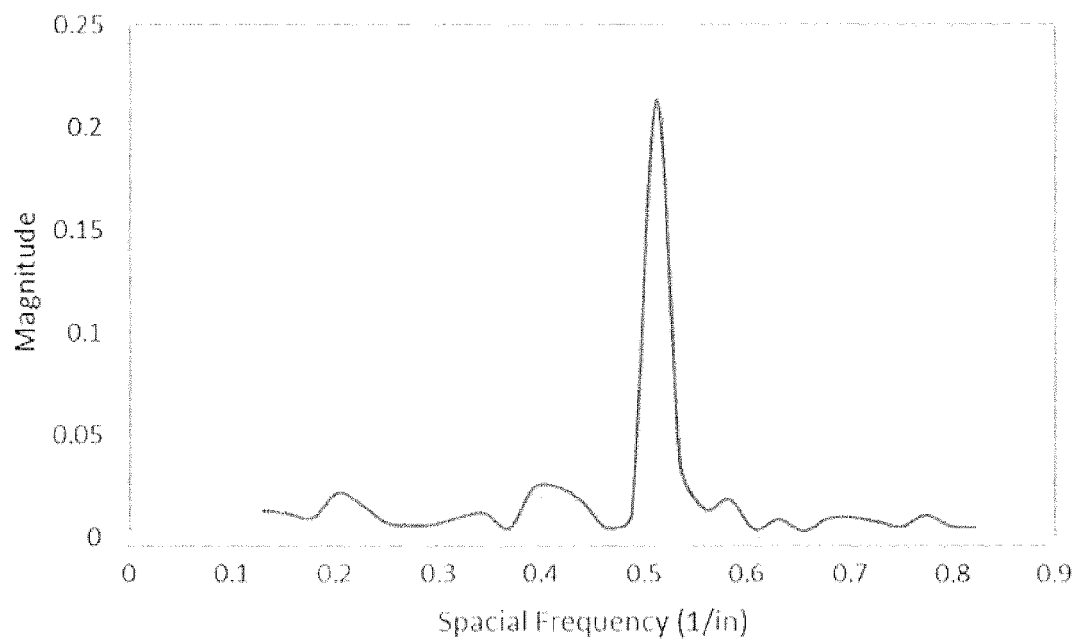
FIG. 17: FFT of sensor output

More broadly, a fast Fourier Transformation (FFT) can be performed on data collected along the length of a rope. When the rope is in new condition the FFT identifies one strong frequency which represents the inverse of the lay length of the rope, as shown in FIG. 17.

The strength member fibers inside the rope will slowly degrade while the rope is used. As the fiber deteriorates, the magnitude of the primary frequency will also diminish. Rope residual strength data can be correlated with this value and a retirement criteria established. A synthetic rope in service could then be monitored with the marked yarn magnetic principle based device (MyMPBD). When the FFT of the output falls below the establish limit the rope should be removed from service.

The data collected in Breakage Detection Mode (BDM) also provides valuable information. This data most closely replicates the standard practice of "counting broken wires" used widely to evaluate wire ropes. A maximum number of broken fibers as a function of linear distance could be used as.I a supplemental retirement criteria.

Rope Data and the MyMPBD Results

Cyclic bending on sheaves (CBOS) testing of aramid rope was used to evaluate MyMPBD and determine if a correlation could be established between its output and rope residual strength.

Figure 18:
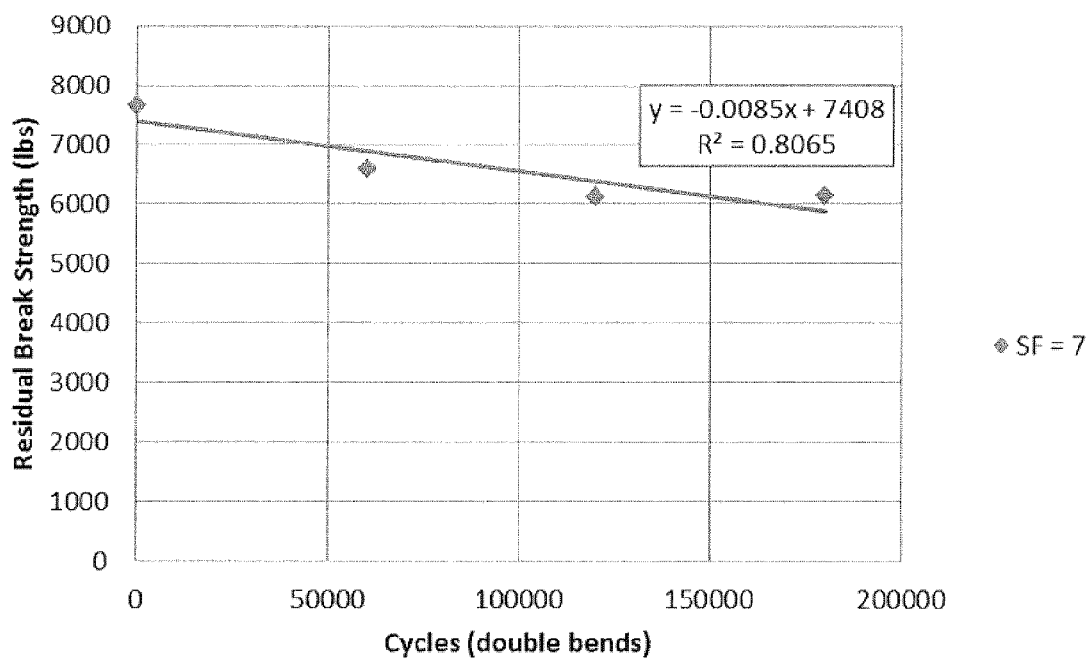
FIG. 18: Residual strength as a function of number of cycles
Figure 19:
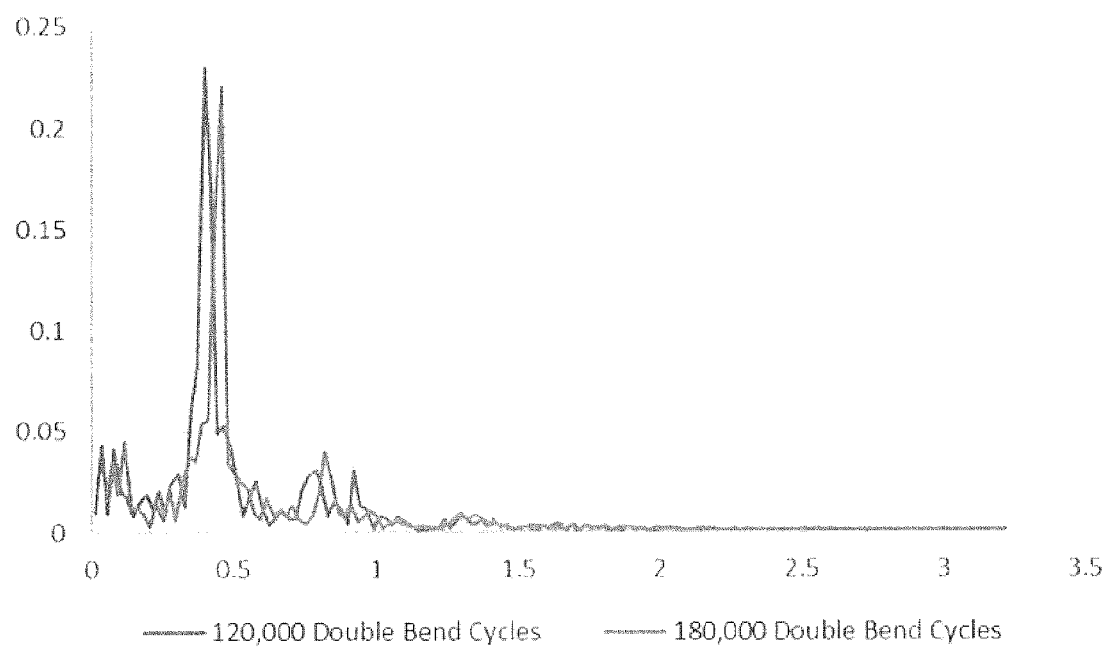
FIG. 19: FFT of MyMPBD data after cycling

The test rope was 0.25" aramid (Twaron" 2200) 6-strand rope construction with load bearing core. The overall jacket of polyester was applied in a twill braid. Samples were cycled on sheaves with D:d of 77:1 and applied tension of 15% MBL, which is representative of a mining application. FIG. 18 shows residual strength of aramid rope as a function of applied cycles. A cycle is defined here as the movement of a section of rope on and then off a sheave. The residual strength data points after 60,000 cycles and 120,000 cycles did not fail in the double bend zone. The data point at 180,000 cycles was a break test result in the double bend zone indicating a loss of strength due to bending fatigue. FFT of LDM data collected on cycles 120,000 and 180,000 is shown in FIG. 19. A gradual change in the shape of the FFT as a function of applied cycles can be observed.

Figure 20:
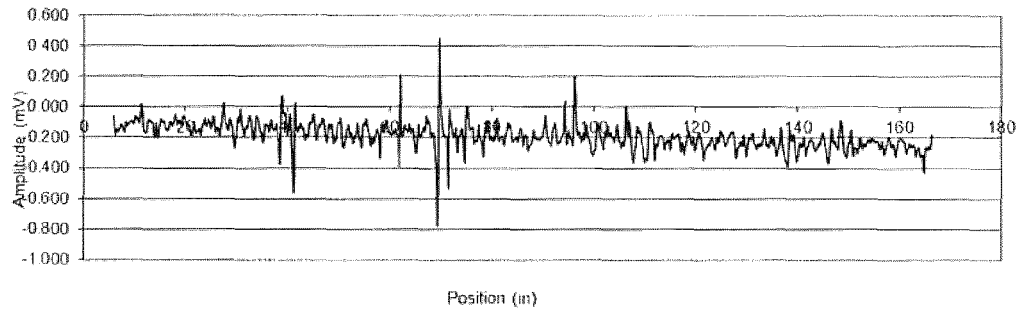
FIG. 20: MyMPBD broken yarn detection along CBOS test sample

The location of the broken elements seen with x-ray imaging were detected with the MyMPBD device in Breakage Detection Mode. (FIG. 20).

Summary of Example 1:

The largest barrier for use of synthetic rope in mine hoisting has been lack of accurate and reliable non-destructive test (NDT) techniques. A multi-faceted inspection approach has been developed and described in this example to monitor synthetic rope, optionally in situ, for this application. This investigation found MyMPBD to be effective means of monitoring internal rope structures while in use.

Marked yarn magnetic principle based detection can be used to detect overall deterioration on synthetic rope and localized damage. If MyMPBD output suggests that an area of the rope has sustained damage, visual inspection and/or x-ray inspection could optionally be used to further analyze the location of interest.

Gradual degradation can also be detected with either MyMPBD inspection. A correlation between the observed deterioration and residual strength can be used to determine when the synthetic rope should be removed from service.

EXAMPLE 2

Scaled CBOS Test Results and MFL Device Output

Introduction

As easily accessible resources near the surface are depleted, the mining industry must go deeper and deeper to reach materials. The current system of steel wire ropes has limitations. At a depth of more than 7,500 feet a steel wire can no longer be used and a second shaft with a second hoist and wire must be installed. The two stage process greatly slows down the extraction of materials and contributes to increased operations costs. This along with many other factors makes synthetic ropes an economically viable alternative to steel wire at greater depths.

Synthetic ropes for mine hoisting are being developed out of an aramid fiber, Twaron. This fiber was chosen for its high strength-to-weight ratio and high elastic modulus. These properties allow a similar diameter and stiffness rope to that of the current steel wire with one-fifth the weight. The fiber also has the advantage of being heat, cut and chemically resistant.

Objective:

To conduct scaled cyclic bend over sheave (CBOS) tests in order to determine the most practical rope construction for reliable and cost effective performance in mine hoisting and assess the magnetic flux leakage (MFL) instrument as a suitable non-destructive testing (NDT) device.

Testing Protocol:

CBOS testing has been conducted on high performance Twaron synthetic ropes on a D:d ratio of 77:1 to simulate a standard two drum mine hoisting system ratio of wire rope diameter versus sheave diameter. The safety factor (SF) at the attachment is of 7.5, again to simulate the typical safety factor used in the mining industry for wire ropes. For the moment and until further development of synthetic ropes can be carried out, the intent is to use the same safety factors (7.5 at the conveyance attachment and 5.0 at the head sheave) for synthetic ropes as compared to the ones used for wire ropes in conformity with the regulation (Québec Regulation). Each series of tests include one sample run at 60,000 cycles, one sample at 120,000 cycles and a last one at 180,000 cycles.

In order to establish the correlation between the number of bending cycles and the residual strength, each of the above mentioned samples was break tested. A new rope that was not been subjected to any bend cycles was also break tested as a control.

Number of Samples Tested:

4 samples of Twaron 1000 (standard yarn)

5 samples of Twaron 2200 (high stiffness yarn)

4 samples of Twaron 2300 (high strength yarn)

After the base case series of 60,000, 120,000 and 180,000 cycles is completed with Twaron 2200, a fifth sample was tested with marker yarns included in the rope to test and evaluate a magnetic flux leakage NDT test device. Output data from the device is then correlated with residual strength test data.

Figure 21:
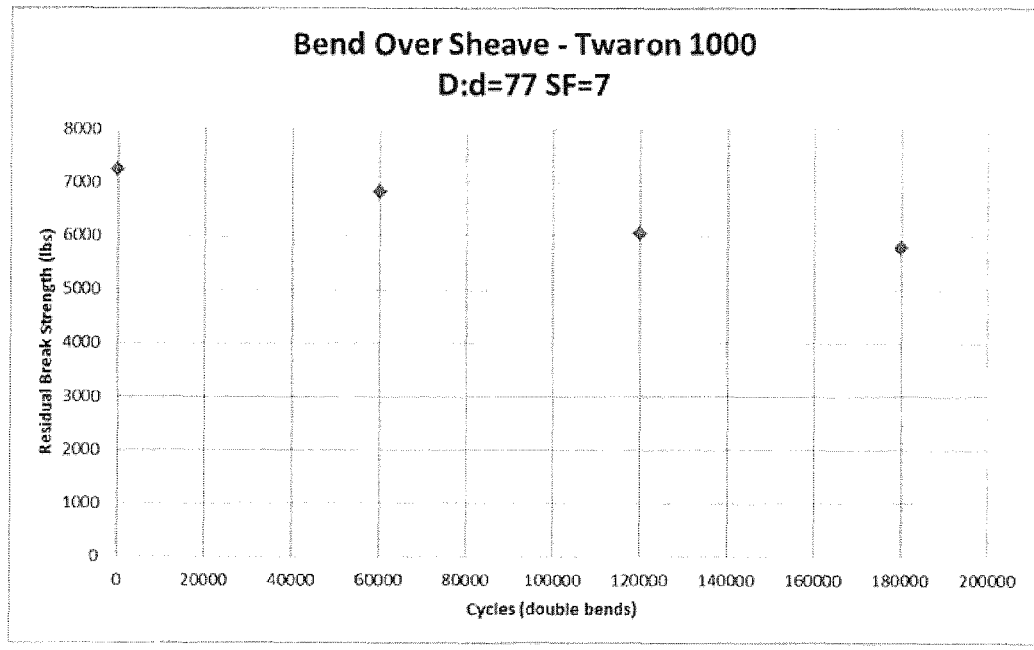
FIG. 21 Twaron™ 1000 bend over sheave test summary. Although the Québec Regulation states a safety factor of 7.5 at the conveyance attachment, a more severe safety factor of 7 was used for all CBOS testing.

CBOS & Residual Strength Tests:

The first set of ropes tested were those made from Twaron 1000. A summary of the rope testing can be seen in FIG. 21 below. Each data point is the peak load recorded during the residual break strength test. For all residual break strength tests, samples were loaded ten times to 1000 lbs. then on the $11_{th}$ cycle the samples were loaded until failure.

For all three Twaron fiber rope sets a rope diameter of ¼ inch was maintained. A sheave of 19¼ inches was used for the bend testing. This gives a constant D:d ratio throughout the testing of 77:1. The three Twaron fibers have different tenacities, so a different test load is used for each. The Twaron 1000 set of bend over sheave testing ropes were under a tension of 1066 lbs.

Figure 22:
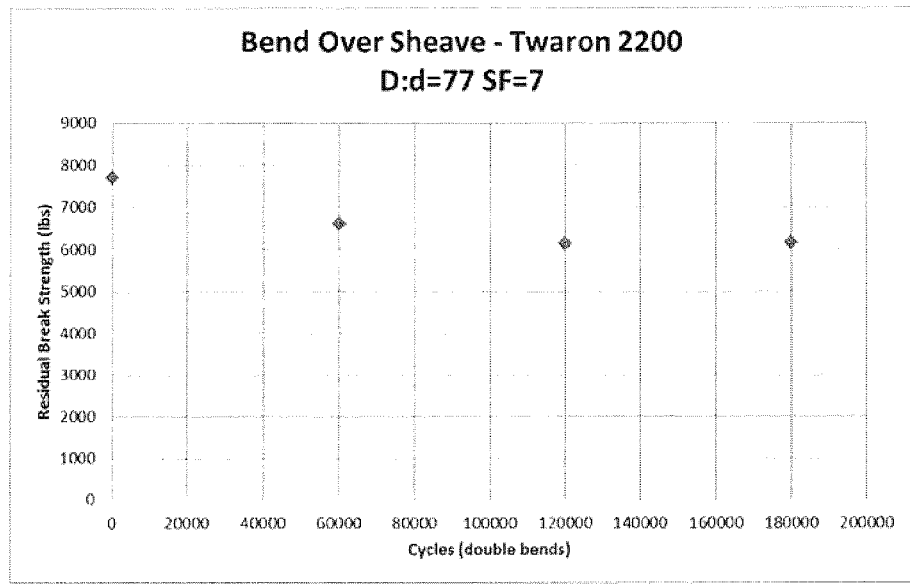
FIG. 22 Twaron 2200 bend over sheave test summary.

A summary of the Twaron 2200 rope testing can be seen in FIG. 22. The D:d ratio remained 77:1 as stated above. To maintain the same factor of safety the bend over sheave test load was lowered to 914 lbs.

Figure 23:
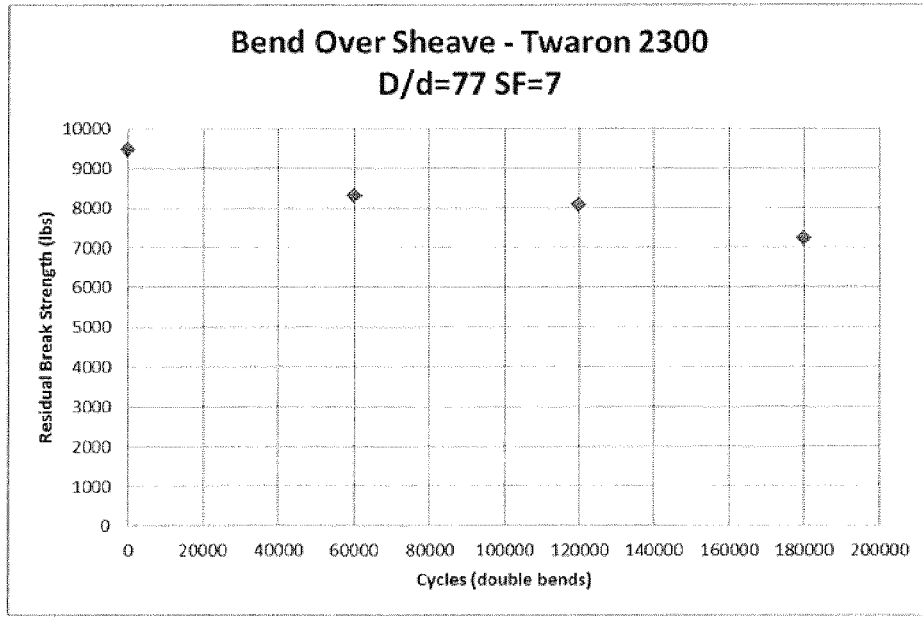
FIG. 23 Twaron 2300 bend over sheave test summary.

A summary of the Twaron 2300 rope testing can be seen in FIG. 23. The D:d ratio remained 77:1 as stated above. To maintain the same factor of safety the bend over sheave test load was raised to 1131 lbs.

Figure 24:
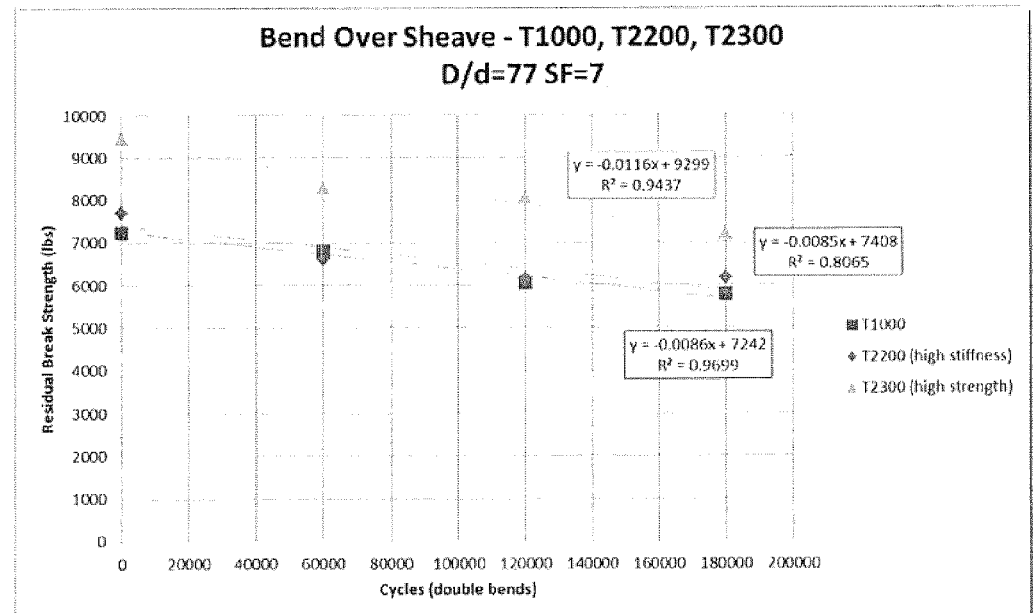
FIG. 24 Twaron 1000, 2200 & 2300 bend over sheave test summary.
Figure 25:
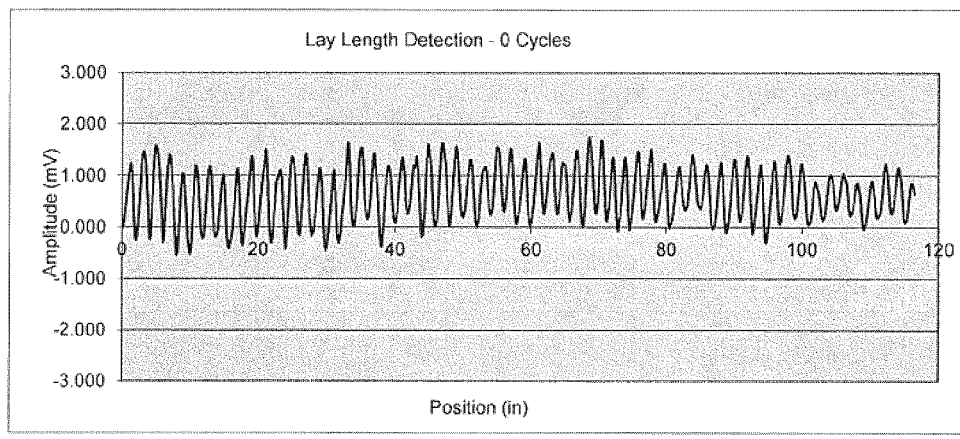
FIG. 25 Lay length detection reading after 0 double bend cycles.
Figure 26:
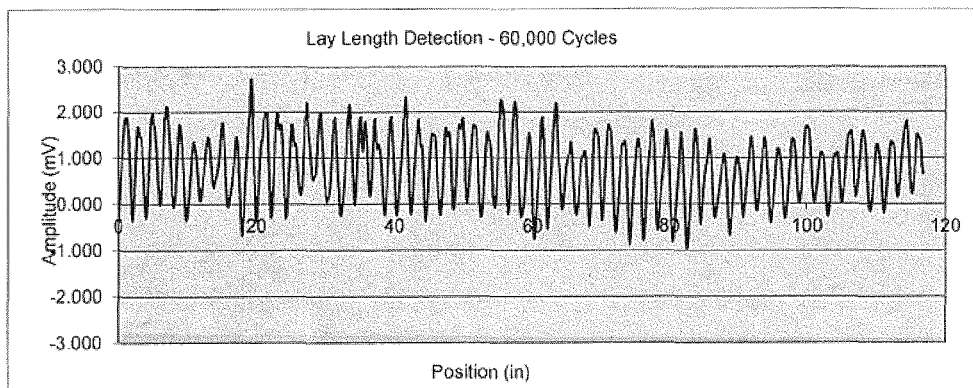
FIG. 26 Lay length detection reading after 60,000 double bend cycles.
Figure 27:
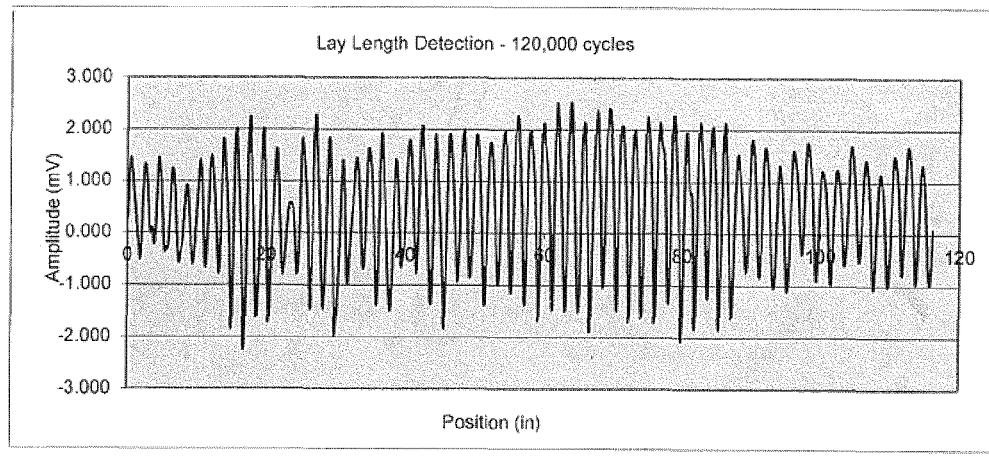
FIG. 27 Lay length detection reading after 120,000 double bend cycles.
Figure 28:
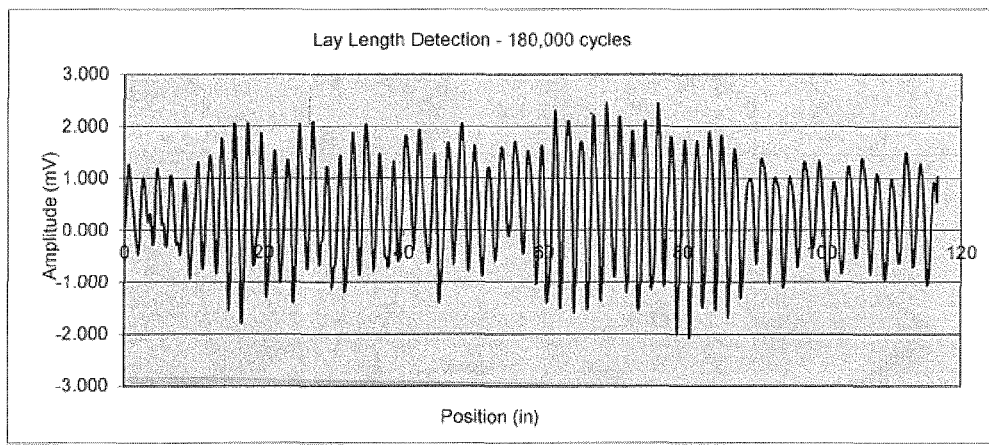
FIG. 28 Lay length detection reading after 180,000 double bend cycles.

A summary of all three rope sets can be seen in FIG. 24. A linear fit is done to each set. The linear nature of the bending fatigue indicates that internal yarn on yarn abrasion is resulting from the fatigue mechanism.

Magnetic Detection NDT

A fifth Twaron 2200 rope sample was manufactured using the same design specifications as the previous Twaron 2200 rope sample, with the addition of a marker fiber. Two ends of Aracon, a nickel plated aramid fiber, were inserted into the rope. This marker fiber can be magnetized and the response sensed by the magnetic flux leakage (MFL) prototype instrument developed by CanmetMINING personnel.

The Twaron 2200 rope with marker fiber was subjected to two readings prior to the bend over sheave testing. One measurement is designed to detect the lay length of the rope. The other is designed to detect any faults in the metallic marker fiber. The rope was tested as is after completion of the manufacturing process.

These same two readings were conducted after 60,000, 120,000, and 180,000 double bend cycles.

Lay Length Detection:

The lay length of the rope is inferred through magnetically detecting the marker fiber within the rope. As rope is passed through the magnetic flux leakage NDT test device, the signal from the marker fiber oscillates. Each oscillation of the signal is a lay of the rope, therefore the local lay length of the rope can be determined by measuring the distance between signal peaks. Lay length detection results are provided below in FIGS. 25-28.

Figure 29:
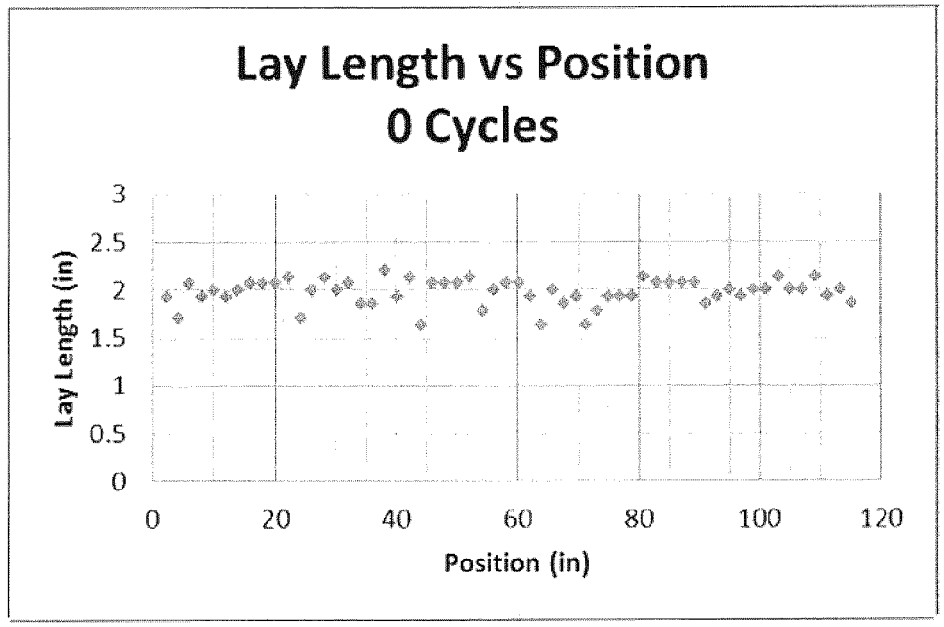
FIG. 29 Rope local lay length after 0 cycles.
Figure 30:
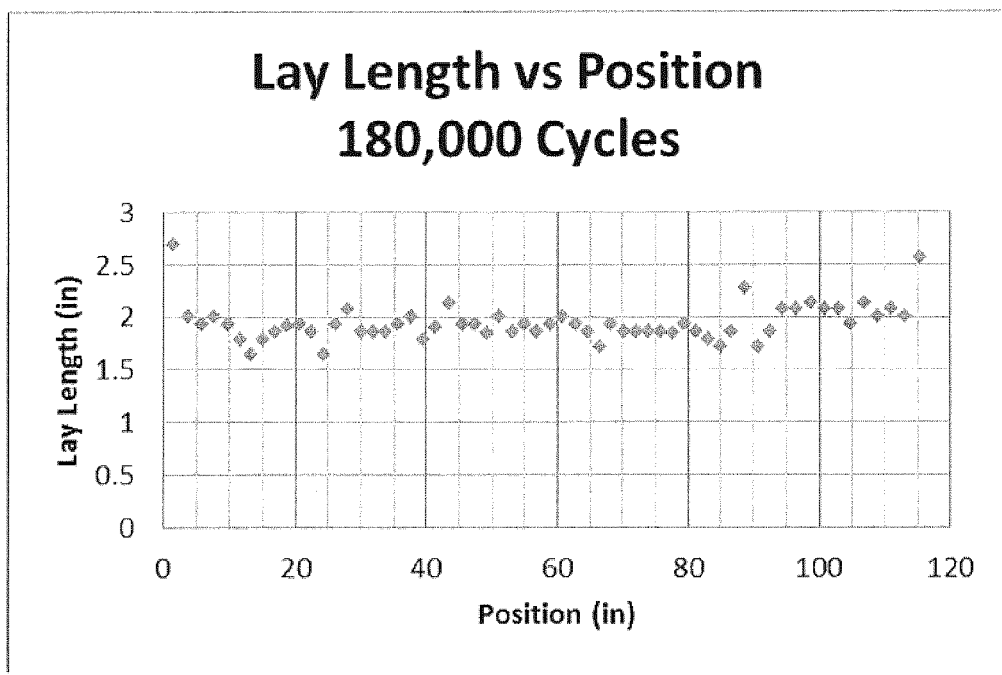
FIG. 30 Rope local lay length after 180,000 cycles.
Figure 31:
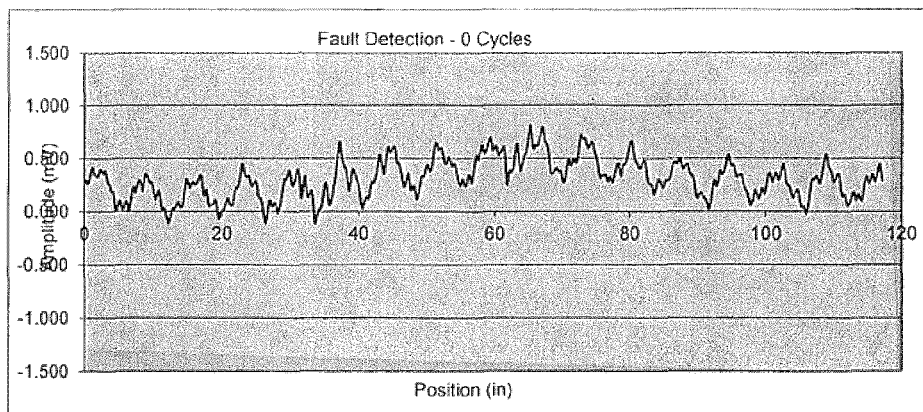
FIG. 31 Fault detection reading after 0 double bend cycles.
Figure 32:
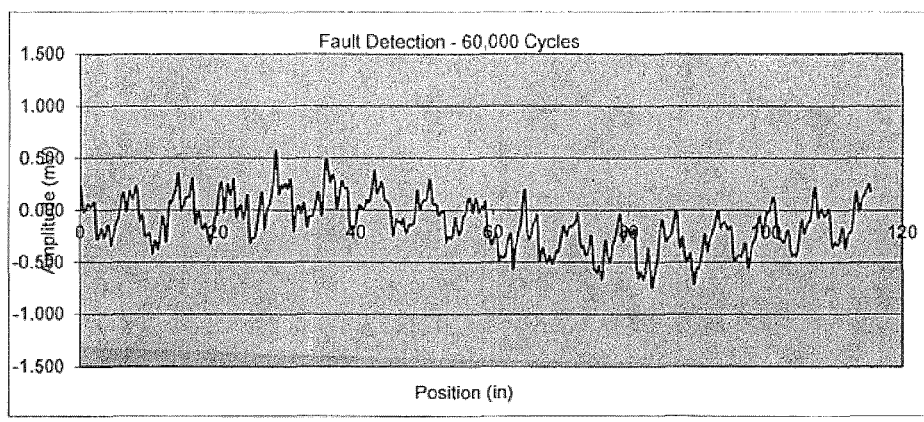
FIG. 32 Fault detection reading after 60,000 double bend cycles.

Ultimately, one objective is to monitor the lay length of the rope, find a correlation between a change in lay length and a change in break strength and use that indicator as a retirement criteria for the rope. An initial comparison of the lay length after 0 cycles and the lay length after 180,000 cycles was done. FIGS. 29 and 30 show the lay length of the rope for the two cases. The lay lengths were determined by taking the difference between the lay length detection peaks.

The rope lay length decreased from 0 to 180,000 cycles. The average lay length went from 1.98" after 0 cycles to 1.94" after 180,000 cycles. The part of the rope that was subjected to bending fatigue was between 10" and 87".

Looking at the 180,000 cycle data alone, the average of the local lay lengths inside this region (the bend zone) is 1.88" and the average of the local lay lengths outside this region is 2.08". With this analysis of the data it appears that the bend fatigue causes the lay length of the rope to shorten locally. This shortening of the lay length can serve as a retirement criteria when properly correlated to loss of strength.

Figure 33:
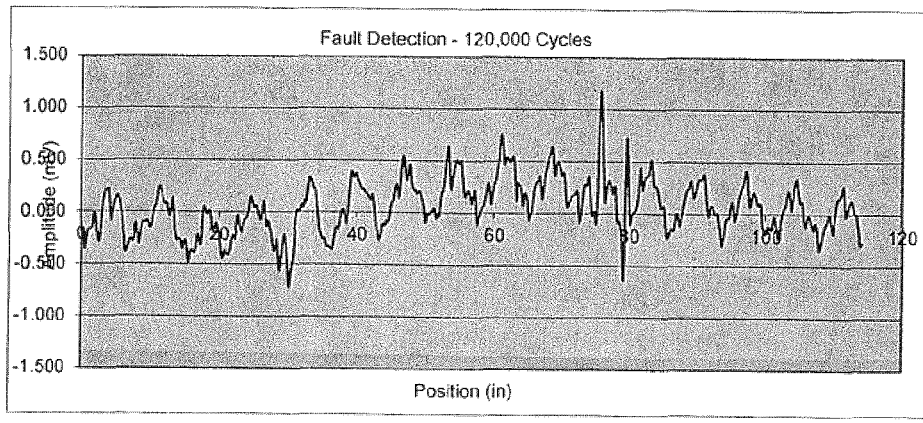
FIG. 33 Fault detection reading after 120,000 double bend cycles.
Figure 34:
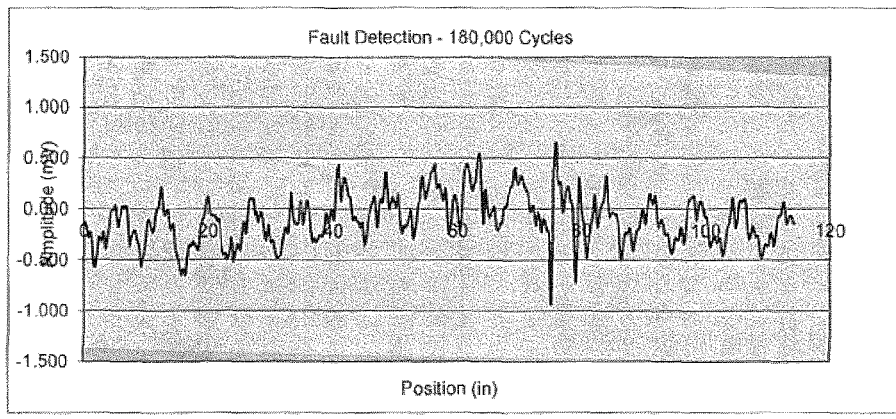
FIG. 34 Fault detection reading after 180,000 double bend cycles.
Figure 35:
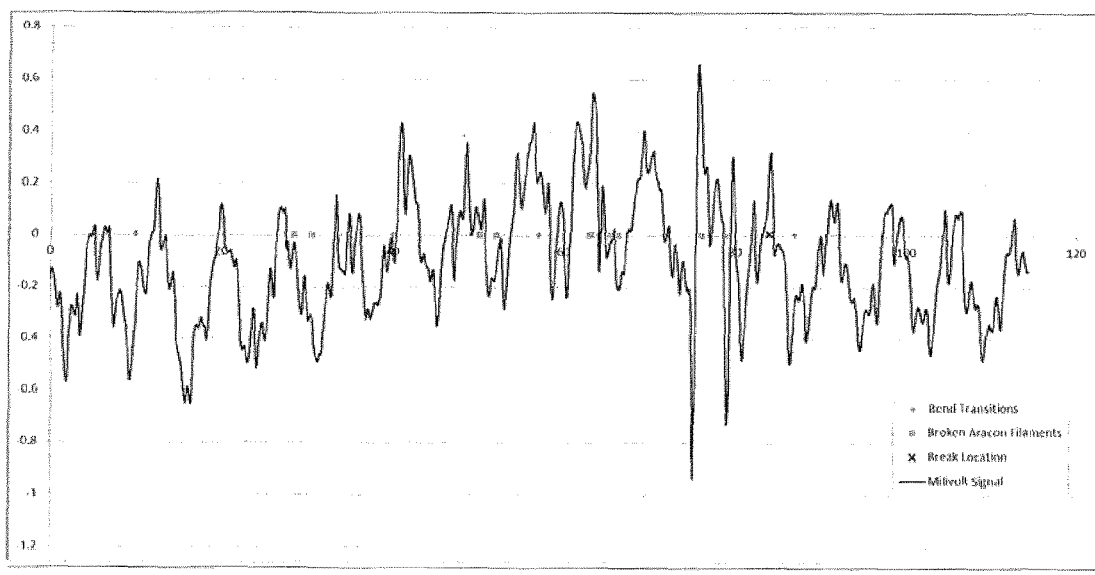
FIG. 35 Twaron 2200 with marker fiber dissection results.

Fault Detection:

The fault detection method developed will create a voltage spike when it passes over a broken metallic element. FIGS. 31-34 show the fault detection signals for various cycle intervals. FIGS. 33 and 34 show two clear voltage spikes at 76" and 79". As discussed in the rope dissection section below, a break in the metallic fiber is not all that is necessary to create a strong enough voltage response when conducting a fault detection reading, there also needs to be some separation between the broken filaments. Without enough separation between the metallic fibers, the amount of magnetic leakage will be insufficient to be detected by the MFL device.

Rope Dissection:

The Twaron 2200 sample with the marker fiber that was subjected to the cyclic bending fatigue and MFL readings discussed above (FIGS. 5-14) was then subjected to a break test. Upon completion of the break test a dissection was conducted. Bend transitions, broken marker fibers, and the location of the rope failure were all recorded as seen in FIG. 15 below. The first bend transition is indicated in FIG. 15 by the blue point at 10". This point represents the transition between the section of the rope that was never on the bending sheave and the section of the rope that went onto the sheave, but didn't come off the sheave in the same cycle (single bend). This point can also be referred to as the single bend transition. There is another single bend transition at 87". The other two bend transitions are at 40" and 57". These bend transitions are referred to as double bend transitions. These are the two points that mark the transition from the single bend to the double bend, where the rope gets on and off the sheave in one cycle. The sample failed about 3 inches inside the single bend transition (similar to most CBOS samples) at 84". This location is close to the locations of the two large signals given off by the fault detection readings at 76" and 79". These signals produced during the fault detection readings may be an indicator of localized weakness, but the signals are not directly on top of the weakest location on the rope. The two large spikes in the fault detection signal correspond to two breaks in the Aracon marker fiber. Although there were breaks in the Aracon throughout the sample only at the locations identified by the two large peaks there was a clear separation between the ends of the Aracon marker fibers. A gap of almost a ¼ inch was measured between the two ends of the Aracon marker fibers. There was no separation between the broken ends of the marker fiber at any other locations along the rope. The marker fiber within the rope may have very quickly developed broken filaments, but only after 120,000 cycles did enough separation occur for a signal to be produced.

Summary of Example 2:

The three rope samples made from Twaron 1000, 2200 and 2300 all displayed a linear loss of strength when subjected to cyclic bending fatigue. The predictable nature of the fatigue will help in the retirement of the rope. The rate of strength loss was similar for all three samples. The Twaron 1000 rope sample lost strength at a rate of 86 lbs/10,000 cycles, the Twaron 2200 lost 85 lbs/10,000 cycles and the Twaron 2300 lost 116 lbs/10,000 cycles. All three rope samples had about a 20% loss of strength over 180,000 cycles.

The local lay length of the rope can be determined using the lay length detection method. A simple comparison of the lay length of the rope initially and after 180,000 cycles was conducted. A change in lay length was observed. The cyclic fatigue shortened the lay length of the rope.

A fault in the metallic marker fiber coupled with local elongation of the rope produced two fault signals using the fault detection method. These signals appeared after 120,000 cycles and were near where the rope failed when subjected to a break strength test.

Whilst various embodiments of methods and apparatuses for rope analysis are described and illustrated herein, the scope of the appended claims is not limited to such embodiments, and the invention encompasses further embodiments readily obtainable in view the teachings presented herein.

REFERENCES

Grabandt, O. "*Engineering with Aramid Fibers*". International Forum on Mine Hoisting, Val d'Or QC. 2010.
Guse, A. "*High Performance Synthetic Ropes for Mine Hoisting*". SME Annual Conference Proceedings. Salt Lake City, Utah. 2013.
Mix, P. Introduction to Nondestructive Testing. Wiley & Sons. USA. 1987.

The invention claimed is:

1. Apparatus for measuring lay length of a synthetic rope comprising at least one magnetic detection element that completes one or more circumferential, helical or sinusoidal path(s) around or within the synthetic rope for each lay length of the synthetic rope, the apparatus comprising:
   a. a sensor device having a body defining an elongate passageway enabling the synthetic rope to be advanced there through in a direction of the central axis of the synthetic rope while permitting limited lateral movements of the synthetic rope;
   b. sensors on the body of the sensor device, sensing changes in magnetic flux in the region of the synthetic rope caused by variations in the magnetic flux of the at least one magnetic detection element and/or its proximity and to the sensors, thereby to generate an oscillating pattern of detected magnetic flux as the synthetic rope advances through the passageway; and
   c. a lay length calculator or display that calculates or displays a distance along the synthetic rope of one or more of the detected oscillations correlating to the number of circumferential, helical or sinusoidal paths of the magnetic detection element around or within the synthetic rope,
   wherein the sensors are spaced circumferentially around the synthetic rope as it is advanced through the passageway, and the signals generated by the sensors are subtractively combined to eliminate components due to any lateral movement of the synthetic rope, the sensors optionally arranged on the sensor device about a common plane transverse to the central axis of the synthetic rope, equidistant from a central axis of the synthetic rope when free of lateral movement in the passageway.

2. The apparatus of claim 1, wherein each of the at least one magnetic detection element comprises a metallic fiber or a synthetic fiber coated with a material detectable by the sensors, the apparatus further comprising means to precondition the at least one magnetic detection element by passing the synthetic rope through a magnetic field at least substantially perpendicular to a direction of movement of the synthetic rope through the sensor device, prior to being passed through the sensor device.

3. The apparatus of claim 2, wherein means to precondition the at least one magnetic detection element comprises one or more permanent magnets, electromagnets or coils, to generate the magnetic field at least substantially perpendicular to the direction of advancement of the synthetic rope through the sensor device, to precondition the at least one magnetic detection element, and wherein the sensors sense changes in the magnetic flux of the at least one pre-conditioned magnetic detection element.

4. The apparatus of claim 1, wherein the sensors are Hall Effect devices, flux gate sensors, or induction coils.

5. The apparatus of claim 1, wherein the sensors are magnetic induction coils formed of electrical wire wound into coils having a clockwise or anticlockwise winding direction, the winding direction of the coils of a first group of sensors all being the same, and the winding direction of the coils of a second group of sensors all being the same but opposite to that of the sensors of the first group, the electrical coils all being interconnected in a single circuit functioning, due to said winding directions of the induction coils of the first and second groups, as a circuit for subtractively combining signals, the output of which is a combined signal for calculation of said lay length.

6. The apparatus of claim 1, wherein the sensor device comprises two separable halves surrounding the passageway to enable the sensor device to be installed around the synthetic rope positioned in said passageway.

7. The apparatus of claim 1, wherein the sensor device further comprises one or more generators of magnetic flux positioned to create a magnetic flux circuit having a part thereof passing through a region of the synthetic rope when present in the passageway, the sensors sensing magnetic flux leakage from the synthetic rope.

8. The apparatus of claim 1, wherein the apparatus is also for detecting breakages in one or more of said at least one magnetic detection elements, the apparatus comprising one or more permanent magnets, electromagnets or coils to generate a magnetic field at least substantially parallel to the direction of advancement of the synthetic rope, to precondition the at least one magnetic detection element so that the sensors sense signals indicative of said breakages.

9. The apparatus of claim 8, wherein the one or more permanent magnets, electromagnets or coils that generate the magnetic field at least substantially parallel to the direction of advancement of the synthetic rope comprise one or more circular permanent magnets.

10. The apparatus of claim 1, wherein the apparatus further comprises:
   a. one or more permanent magnets, electromagnets or coils, to generate a magnetic field at least substantially perpendicular to the direction of advancement of the synthetic rope through the sensor device, to precondition the at least one magnetic detection element so that the sensors sense a lay length of the synthetic rope; and
   b. one or more permanent magnets, electromagnets or coils, to generate a magnetic field at least substantially parallel to the direction of advancement of the synthetic rope, to precondition the at least one magnetic detection element so that the sensors sense signals indicative of breakage or damage to the elements.

11. The apparatus of claim 1 that is also for testing the synthetic rope for breakage points or damage to the at least one magnetic detection element, wherein the sensors on the body of the sensor device also sense changes in magnetic flux in the region of the synthetic rope caused by breakage or damage to the at least one magnetic detection element, the calculator or display further calculating or displaying recorded data corresponding to the changes in magnetic flux resulting from said breakage or damage.

12. Apparatus for testing a synthetic rope comprising at least one magnetic detection element running the length of the synthetic rope, the apparatus comprising:
   a. a sensor device having a body defining an elongate passageway enabling the synthetic rope to be advanced therethrough in a direction of the central axis of the synthetic rope while permitting limited lateral movements of the synthetic rope;
   b. sensors on the body of the sensor device, sensing changes in magnetic flux in the region of the synthetic rope caused by breakage points or damage to the at least one magnetic detection element; and
   c. a calculator or display that calculates or displays recorded data corresponding to the changes in magnetic flux,
   wherein the sensors are spaced circumferentially around the synthetic rope as it is advanced through the passageway, and the signals generated by the sensors are subtractively combined to eliminate components due to any lateral movement of the synthetic rope, the sensors optionally arranged on the sensor device about a common plane transverse to the central axis of the synthetic rope, equidistant from a central axis of the synthetic rope when free of lateral movement in the passageway.

13. Use of the apparatus of claim 1 for testing a synthetic rope comprising at least one magnetic detection element, to assess at least one of: the integrity, the strength, the safety, the lifespan, the load capacity, the wear, the lay length, faults or breakages of the at least one magnetic detection element, of the synthetic rope or portions thereof.

14. A method for testing a lay length of a synthetic rope comprising at least one magnetic detection element running through or about the synthetic rope, the method comprising the steps of:
   a. applying the apparatus of claim 1 to the synthetic rope, so that the synthetic rope passes through the passageway of the sensor device;
   b. advancing the synthetic rope through the passageway so that the sensors on the body of the sensor device sense changes in magnetic flux in the region of the synthetic rope caused by variations in the proximity and magnetic flux of the magnetic detection element to the sensors, thereby to generate an oscillating pattern of detected magnetic flux as the synthetic rope advances through the passageway;
   c. associating the detected oscillations with physical distances along the synthetic rope; and
   d. calculating or displaying a lay length according to a distance along the synthetic rope of one or more of the detected oscillations correlating to the number of circumferential, helical or sinusoidal paths of the magnetic detection element around or within the synthetic rope,
   wherein the sensors are spaced circumferentially around the synthetic rope as it is advanced through the passageway, and the signals generated by the sensors are subtractively combined to eliminate components due to any lateral movement of the synthetic rope, the sensors optionally arranged on the sensor device about a common plane transverse to the central axis of the synthetic rope, equidistant from a central axis of the synthetic rope when free of lateral movement in the passageway.

15. The method of claim 14, further comprising a step of:
   pre-conditioning the at least one magnetic detection element of the synthetic rope by passing the synthetic rope through a magnetic field at least substantially perpendicular to a direction of movement of the synthetic rope through the sensor device.

16. The method of claim 15, wherein in the step of pre-conditioning the field at least substantially perpendicular to a direction of movement of the synthetic rope is generated by one or more permanent magnets, electromagnets or coils.

17. The method of claim 14, wherein the sensors are Hall Effect devices, flux gate sensors, or induction coils.

18. The method of claim 17, wherein the sensors are magnetic induction coils formed of electrical wire wound into coils having a clockwise or anticlockwise winding direction, the winding direction of the coils of a first group of sensors all being the same, and the winding direction of the coils of a second group of sensors all being the same but opposite to that of the sensors of the first group, the electrical coils all being interconnected in a circuit functioning, due to said winding directions of the induction coils of the first and second groups, as a circuit for subtractively combining signals, the output of which is a combined signal for calculation of said lay length.

19. The method of claim 14, wherein the sensor device comprises two separable halves surrounding the passageway, the step of applying the apparatus to the synthetic rope comprising at least partially separating the separable halves to install the halves about the synthetic rope such that the synthetic rope runs through said passageway.

20. The method of claim 14, further comprising creating a magnetic flux circuit having a part thereof passing through a region of the synthetic rope when present in the passageway, from one or more generators of magnetic flux, the sensors sensing magnetic flux leakage from the synthetic rope.

21. The method of claim 14, further comprising creating eddy currents in the at least one magnetic detection element, the sensors sensing magnetic fields produced by the eddy currents.

22. The method of claim 14, further comprising generating a magnetic field at least substantially parallel to the direction of advancement of the synthetic rope, to precondition the at least one magnetic detection element so that the sensors sense signals indicative of breakages in one or more of said at least one magnetic detection elements.

23. The method of claim 22, wherein the magnetic field at least substantially parallel to the direction of advancement of the synthetic rope is generated by one or more permanent magnets, electromagnets or coils, preferably one or more circular permanent magnets.

24. The method of claim 14, wherein the method further comprises:
   a. generating, with one or more permanent magnets, electromagnets or coils, a magnetic field at least substantially perpendicular to the direction of advancement of the synthetic rope through the sensor device, to precondition the at least one magnetic detection element so that the sensors sense a lay length of the synthetic rope; and
   b. generating, with one or more permanent magnets, electromagnets or coils, a magnetic field at least substantially parallel to the direction of advancement of the synthetic rope, to precondition the at least one magnetic detection element so that the sensors sense signals indicative of said breakages.

25. The method of claim 24, wherein the step of advancing comprising movement of the synthetic rope through the passageway in both axial directions in any order, optionally repeated, the one or more permanent magnets, electromagnets or coils of a. positioned on one side of the sensors such that the at least one magnetic detection element is preconditioned for lay length detection when the synthetic rope is advanced a first way though the passageway, and the one or more permanent magnets, electromagnets or coils of b. are positioned on an opposite side of the sensors from the permanent magnet(s) of a. so that the synthetic rope is preconditioned for breakage detection when advanced through the passageway in a second direction opposite to the first direction.

26. A method for testing a synthetic rope comprising at least one magnetic detection element running the length of the synthetic rope, the method comprising the steps of:
 a. applying to the synthetic rope an apparatus of claim 12, such that the rope passes through the elongate passageway;
 b. advancing the synthetic rope through the passageway, the sensors sensing changes in magnetic flux in the region of the synthetic rope caused by breakage or damage to the at least one magnetic detection element; and
 c. calculating or displaying data corresponding to the changes in magnetic flux indicative of said breakages or damage to the at least one magnetic detection element.

* * * * *